United States Patent [19]
Laufer et al.

[11] Patent Number: 5,939,415
[45] Date of Patent: *Aug. 17, 1999

[54] [A]-ANNELLATED PYRROLE DERIVATIVES AND THEIR USE IN PHARMACOLOGY

[75] Inventors: Stefan Laufer; Hans Günther Striegel, both of Blaubeuren; Gerd Dannhardt, Mainz, all of Germany

[73] Assignee: Merckle GmbH, Blaubeuren, Germany

[ * ] Notice: This patent is subject to a terminal disclaimer.

[21] Appl. No.: 08/737,920

[22] PCT Filed: May 31, 1995

[86] PCT No.: PCT/EP95/02078

§ 371 Date: Mar. 28, 1997

§ 102(e) Date: Mar. 28, 1997

[87] PCT Pub. No.: WO95/32971

PCT Pub. Date: Dec. 7, 1995

[30] Foreign Application Priority Data

Jun. 1, 1994 [DE] Germany ................ 44 19 315

[51] Int. Cl.$^6$ ............. C07D 413/02; C07D 417/02; A61K 31/505; A61K 31/535

[52] U.S. Cl. ............. 514/224.2; 514/183; 514/211; 514/224.2; 514/230.5; 514/258; 514/368; 514/375; 514/393; 540/552; 540/579; 544/47; 544/90; 544/282; 548/152; 548/159; 548/179; 548/180; 548/217; 548/302.7

[58] Field of Search ................ 548/173–174, 548/180, 152, 221, 217, 302.7, 159, 179; 514/368, 375, 393, 387, 183, 211, 224.2, 230.5, 258; 544/47, 90, 282

[56] References Cited

U.S. PATENT DOCUMENTS

| | | | |
|---|---|---|---|
| 3,920,672 | 11/1975 | Untch et al. | 514/368 |
| 4,536,512 | 8/1985 | Biftu et al. | 514/368 |
| 4,684,658 | 8/1987 | Fabre et al. | 514/338 |
| 5,552,422 | 9/1996 | Gauthier et al. | 514/368 |

FOREIGN PATENT DOCUMENTS

| | | |
|---|---|---|
| A-0 397 175 | 11/1990 | European Pat. Off. . |
| 608133 | 7/1994 | European Pat. Off. . |
| A-24 19 071 | 11/1974 | Germany . |

OTHER PUBLICATIONS

Pyl et al., *Justus Liebigs Annalen der Chemie*, 679, 1964, 139–144.
Molloy et al., *Journal of the Chemical Society*, 1965, 65–71.
Galera et al., *Journal of Heterocyclic Chemistry*, 23, 1986, 1889–1892.
Buchen et al., *Journal of Organic Chemistry*, 42(14), 1977, 2448–2454.
Meyers et al., *Chemical Abstracts*, 76(3), 1972, abstract No. 14391j.
Kibirev et al., *Chemical Abstracts*, 61(1), 1964, abstract No. 5629g.
Weuffen et al., *Chemical Abstracts*, 64(1), 1966, abstract No. 5488e.
Alekseeva, *Chemical Abstracts*, 84(17), 1976, abstract No. 120952t.
Druzhinina et al., *Chemical Abstracts*, 80(25), 1974, abstract No. 146165f.
Druzhinina et al., *Chemical Abstracts*, 68(11), 1968, abstract No. 49510j.
Ceder et al., *Chemical Abstracts*, 77(19), 1972, abstract No. 126481r.
Druzhinina et al., *Chemical Abstracts*, 77(13), 1972, abstract No. 88394e.
Alekseeva et al., *Chemical Abstracts*, 77(9), 1972, abstract No. 61153p.
Druzhinina et al., *Chemical Abstracts*, 86(17), 1977, abstract No. 121252t.
Brindley et al., *Chemical Abstracts*, 106(19), 1987, abstract No. 156332c.
Druzhinina et al., *Chemical Abstracts*, 87(1), 1977, abstract No. 5863q.

*Primary Examiner*—Matthew V. Grumbling
*Attorney, Agent, or Firm*—Bacon & Thomas

[57] ABSTRACT

The present invention relates to heterocyclic compounds with the formula

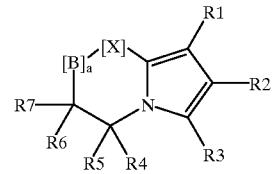

in which $R^1$ to $R^7$, B, a, and X have the meanings indicated in the specification. These compounds can be used for the treatment of diseases of the rheumatic variety and for the prevention of allergically-induced diseases.

15 Claims, 9 Drawing Sheets

[A]-ANNELLATED PYRROLE DERIVATIVES AND THEIR USE IN PHARMACOLOGY

The invention relates to pyrroles which are anellated at bond a and their use in pharmacology as well as pharmaceuticals that contain these compounds.

It is known that arachidonic acid is metabolized by two different routes. In the cyclooxygenase path, arachidonic acid is metabolized into prostaglandins through the influence of the enzyme cyclo-oxygenase. In the lipoxygenase path, arachidonic acid is metabolized into so-called leukotrienes through the influence of lipoxygenases.

Prostaglandins are involved in the development of inflammation, fever, and pain, while leukotrienes play an important role in the development of asthma, inflammations, and allergies. To combat these symptoms, often nonsteroidal anti-inflammatory drugs are used such as arylethanoic acid derivatives, 2-arylpropionic acid derivatives and anthranilic acid derivatives. These derivatives inhibit cyclooxygenase and consequently prevent the formation of prostaglandins from arachidonic acid. Such derivatives, though, are not used without reservations with regard to their side effects. Drugs that inhibit the lipoxygenase are not available on the market.

European Patent Disclosure EP-A-397 175 describes pyrrolizine compounds with the formula:

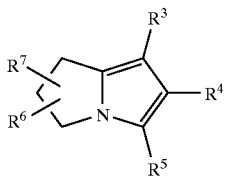

in which two of the radicals $R^3$, $R^4$, and $R^5$ independently stand for H, $C_5$–$C_8$ cycloalkyl, $C_1$–$C_{12}$ alkyl or aryl, which is optionally substituted by one or two radicals which are selected from the group comprising halogen, $NO_2$, $C_1$–$C_4$ alkoxy, hydroxy, $C_1$–$C_4$ alkyl or phenoxy, and the third of the radicals $R^3$, $R^4$, and $R^5$ stands for CHO, $CO_2HO$, $COSC_1$–$C_4$ alkyl, or A—X, where A stands for a straight-chain or branched $C_1$–$C_8$ alkylene group or a $C_2$–$C_8$ alkenylene group and X stands for $CO_2H$, $SO_3H$, CHO, OH, or SH. These compounds are cyclooxygenase and/or lipoxygenase inhibitors and can therefore be used in the treatment of diseases of the rheumatoid variety and for the prevention of allergically induced diseases.

Surprisingly, it has now been discovered that certain heterocyclic compounds are superior to the above-described pyrrolizine compounds in their effect and in particular in the inhibition of lipoxygenase.

The subject of the invention, therefore, are heterocyclic compounds of formula I:

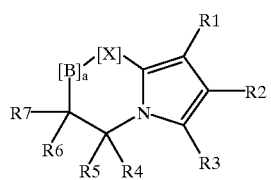

in which two of the radicals $R^1$, $R^2$, and $R^3$, which may be identical or different, stand for a hydrogen atom, an aryl radical which optionally has one or two substituents that are selected from the group comprising halogen, pseudohalogen, $CF_3$, $NO_2$, OH, alkoxy, $OCF_3$, alkyl, and aryloxy, or for a monocyclic or bicyclic, aromatic, heterocyclic radical which has at least one oxygen, nitrogen, and/or sulfur atom and which is optionally condensed with a phenyl or naphthyl radical and is optionally substituted by halogen, $CF_3$, alkyl, or alkoxy and the third of the radicals $R^1$, $R^2$, and $R^3$ stands for H, CHO, $CO_2H$, COO alkyl, COS alkyl, $COCO_2H$, $COCO_2$ alkyl, or A—Y, A stands for $C_1$–$C_8$ alkylene or $C_2$–$C_8$ alkenylene, Y stands for $CO_2H$, $SO_3H$, $OPO(OH)_2$, $OP(OH)_2$, a group that represents an acid equivalent, COO alkyl, $SO_2O$ alkyl, CHO, OH, or $CONR^8R^9$, $R^8$ and $R^9$, which may be identical or different, stand for H, alkyl, OH, acyl, $SO_2$ alkyl, or $SO_2$ phenyl, where the alkyl radical of the sulfonyl group is optionally substituted by one or more halogen atoms and the aryl radical is optionally substituted by one or more halogen, $C_1$–$C_8$ alkyl, or $C_1$–$C_8$ alkoxy radicals, $R^4$, $R^5$, $R^6$, and $R^7$, which may be identical or different, stand for H, alkyl, Y, or A—Y according to the above definition, or two of the vicinal radicals stand for a chemical bond between the two ring atoms to which they are bonded, and the other two have the meanings stated or two of the geminal radicals, together with the carbon atom to which they are bonded, stand for a carbonyl group or its thio analog, X stands for O, S, SO, $SO_2$, CO, or $NR^{10}$, where $R^{10}$ stands for H, alkyl, A—Y according to the above definition, or aryl which is optionally substituted by halogen, $C_1$–$C_8$ alkyl or $C_1$–$C_8$ alkoxy, B stands for $CR^{11}R^{12}$, where $R^{11}$ and $R^{12}$, which may be identical or different, stand for H, alkyl, Y, or A—Y, and A and Y have the meanings stated, or $R^{11}$ and $R^{12}$, together with the carbon to which they are bonded, stand for a carbonyl group or its thio analog, and a stands for 0, 1, or 2, and their optical isomers, salts, and esters.

The pharmaceutically compatible salts in the present case can be acid addition salts or base addition salts. Inorganic acids such as hydrochloric acid, sulfuric acid, or phosphoric acid, or organic acids such as tartaric acid, lactic acid, citric acid, malic acid, mandelic acid, ascorbic acid, maleic acid, fumaric acid, gluconic acid, and the like are used for acid addition salts.

Base addition salts include salts of the formula I compounds with inorganic bases such as sodium hydroxide or potassium hydroxide or with organic bases such as monoethanolamine, diethanolamine, or triethanolamine.

The esters of the formula I compounds, in particular include esters that are physiologically easy to hydrolyze, for example alkyl ester, pivaloyloxymethyl ester, acetoxymethyl ester, phthalidyl ester, indanyl ester, and methoxymethyl ester.

The term "alkyl, alkoxy, etc." includes straight-chain or branched alkyl groups such as methyl, ethyl, n-propyl and i-propyl, n-butyl, i-butyl, or t-butyl, n-pentyl, neopentyl, n-hexyl, etc.

Unless otherwise indicated, "alkyl" preferably stands for $C_1$–$C_8$ alkyl, in particular for $C_1$–$C_6$ alkyl, and in particular preferably, for $C_1$–$C_4$ alkyl.

"Aryl" preferably stands for naphthyl and in particular for phenyl.

The term "halogen atom" includes a fluorine, chlorine, bromine, or iodine atom and in particular for a fluorine or chlorine atom. "Pseudohalogen" particularly stands for CN, OCN, SCN, or $N_3$.

"Alkylene" or "alkenylene" stands for straight-chain or branched alkylene or alkenylene groups with preferably 1 to 6 or 2 to 6 and in particular 1 to 4 or 2 to 4 carbon atoms. The alkylene group and in particular the methylene group is preferable.

"Acyl" stands for RCO, where R preferably has the meanings stated for "alkyl" and "aryl". Acetyl is particularly preferable.

In particular, a group which represents an acid equivalent is the tetrazolyl group.

The "aromatic, heterocyclic radical" refers in particular to a 5 and 6-member heterocyclic radical that can be substituted and anellated as indicated above. Examples are a thiophene, pyrrole, imidazole, thiazole, thiadiazole, furan, oxazole, isoxazole, pyridine, pyrimidine, benzofuran, or quinoline radical. If the heterocycle is substituted, 1, 2, or 3 substituents are available, which are selected from the group comprising halogen, $C_1$–$C_8$ alkyl, and $C_1$–$C_8$ alkoxy. Thiophene and halogen-substituted thiophene, in particular chlorine-substituted thiophene, are preferable.

The substituents of the aryl group are preferably selected from the group comprising halogen, in particular fluorine or chlorine, $CF_3$, $NO_2$, and phenoxy. If the aryl group is a phenyl ring, the substituents are preferably situated in the m-position and/or the p-position.

If Y stands for $CONR^8R^9$, then $R^8$ preferably stands for a hydrogen atom and $R^9$ stands for optionally halogen-substituted $SO_2C_1$–$C_8$ alkyl or optionally $C_1$–$C_8$ alkyl-substituted $SO_2$ phenyl, in particular $SO_2CH_3$, $SO_2CF_3$, $SO_2$ phenyl or $SO_2$ toluyl.

Preferably the third of the radicals $R^1$, $R^2$, and $R^3$ is situated in the 5-position of the pyrrolizidine structure.

One set of preferred embodiments is the compounds of the above-mentioned formula I, in which two of the radicals $R^1$, $R^2$, and $R^3$ independently stand for H, phenyl, halogen, or $CF_3$-substituted phenyl (one, two, or three halogen atoms) or a 5- or 6-member heterocyclic ring of the above-defined type, and the third of the radicals $R^1$, $R^2$, and $R^3$ stands for A—Y, where A stands for $C_1$–$C_8$ alkylene and Y stands for $CO_2H$, $COOC_1$–$C_8$ alkyl, $SO_3H$, $SO_2OC_1$–$C_8$ alkyl, CHO, $COCO_2H$, $COCO_2C_1$–$C_8$ alkyl, or $CONR^8R^9$, where $R^8$ and $R^9$ have the meanings stated and in particular, stand for H, alkyl, $SO_2$ alkyl or $SO_2$ phenyl, optionally with the above-mentioned substituents.

Another set of preferable embodiments is the compounds of the above-mentioned formula I, in which $R^1$ stands for H or phenyl, $R^2$ stands for phenyl, halogen-substituted phenyl, or a 5- or 6-member heterocyclic ring, and $R^3$ stands for A—Y, where A and Y have the meanings stated.

In a particularly preferable manner, A—Y stands for $CH_2COOH$ or $CH_2CONHSO_2R$, where R stands for $CH_3$, $CF_3$, phenyl, or tolyl.

A particularly preferable set of embodiments is the compounds of the above-mentioned formula I, in which two of the radicals $R^4$ and $R^6$ or $R^5$ and $R^7$ together stand for a chemical bond or in which the radicals $R^4$–$R^7$ stand for H or alkyl. These compounds have the formula:

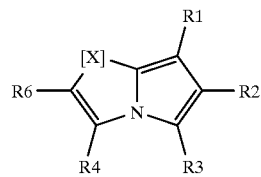

and

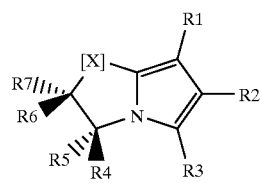

The radicals $R^1$ to $R^7$ and X have the meanings stated.

X preferably stands for O, S, SO, $SO_2$, or $NR_1$ and in particular for S, SO, $SO_2$.

B preferably stands for $CH_2$ or $CH_2CH_2$;

a preferably stands for 0 or 1, in particular for 0.

If the compounds according to the invention have asymmetry centers, racemates as well as optical isomers (enantiomers, diastereomers) are included.

The synthesis of the compounds according to the invention takes place analogous to the processes A to O described in FIGS. 1–5. These are partially described in European Patent Disclosure EP-A-397 175; reference is hereby made to this publication and the literature references mentioned therein.

Initial compounds for the production of the compounds according to the invention are the compounds of formula II:

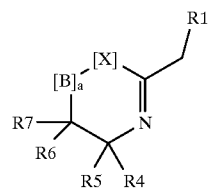

where $R^1$, $R^4$ to $R^7$, $[B]_a$ and X have the meanings stated.

These compounds are known in the literature or they can be produced analogous to known processes, for example through the reaction of aminothiols, diamines, and amino alcohols derived from D- and L-amino acids, with the imide esters of correspondingly substituted carboxylic acids (FIG. 1b A1/A2).

The formula II compounds are reacted with the corresponding compounds of formula III:

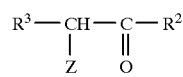

in which Z stands for Cl or Br and $R^2$ and $R^3$ have the desired meanings. The formula III compounds are likewise known from the literature or they can be produced analogous to known processes, for example those compounds in which $R^2$ stands for an aromatic, heterocyclic radical are produced analogous to the processes described by J. J. Riehl in C. R. Hebd. Seance. Acad. Sci. Ser. C (1957), 245, pp. 1321–1322.

The reaction according to process A preferably takes place in an ether or aromatic hydrocarbon, e.g. diethyl ether, benzene, or toluene. As a rule, the intermediarily produced quaternizing product precipitates out. It is isolated under conditions of water exclusion and then, in an inert solvent, e.g. dichloromethane, is treated with base, e.g. triethyl amine. The reaction temperature is not critical, it generally lies in the range between room temperature and the boiling temperature of the solvent.

This reaction produces the formula Ia compounds:

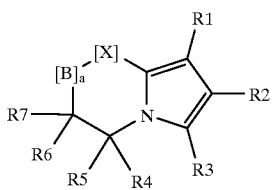

Ia

If at least one of the radicals $R^1$, $R^2$, and $R^3$ stands for a hydrogen atom, compounds of the following formulas are obtained:

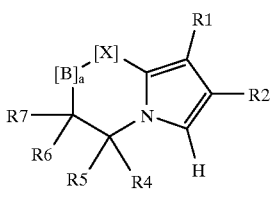

IVa

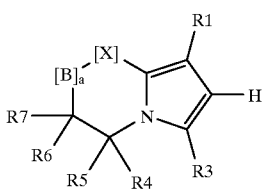

IVb

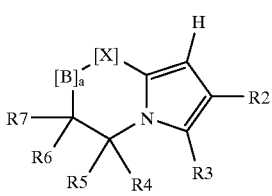

IVc

The compounds of series a, b, or c are derived from this depending on the position of the hydrogen atom.

BRIEF DESCRIPTION OF THE DRAWINGS

This reaction as well as the reactions mentioned below are outlined in FIGS. 1a–c, 2, 3a, 3b, 4, 5a, and 5b in the example of the compounds of series a. The same is true for the synthesis and derivative production of the compounds of series b and c.

In addition to the process described in European Patent Disclosure EP-A-397 175 (process A), another process (process B) is used for the composition of heterocycles IVa, IVb, and IVc (FIG. 2): the starting point of this process is correspondingly substituted 2-(5H)furanones (VI), which are produced from carboxylic acid salts of structure V and the halogen aldehydes and halogen ketones of structure III (FIG. 2), analogous to the methods described in the literature (a: Rio, G. and Sekiz, B. Bull. Soc. Chim. Fr. 1976, 1491, 1495. b: Padwa, A., Brookhart, T., Dehm, D., and Wubbels, G., J. Am. Chem. Soc. 1978, 100, 8247, 8259). Analogous to methods known from the literature, these are transformed into 1,5-dihydro-2-pyrrolones (VII or VIII) (c: Matsuda et al. Yakugaku Zasshi 95, [1975] 190, 194 (C. A. 83 [1975] 42 780; d: Rio, G. and Sekiz, B., see above).

Figure 1A:
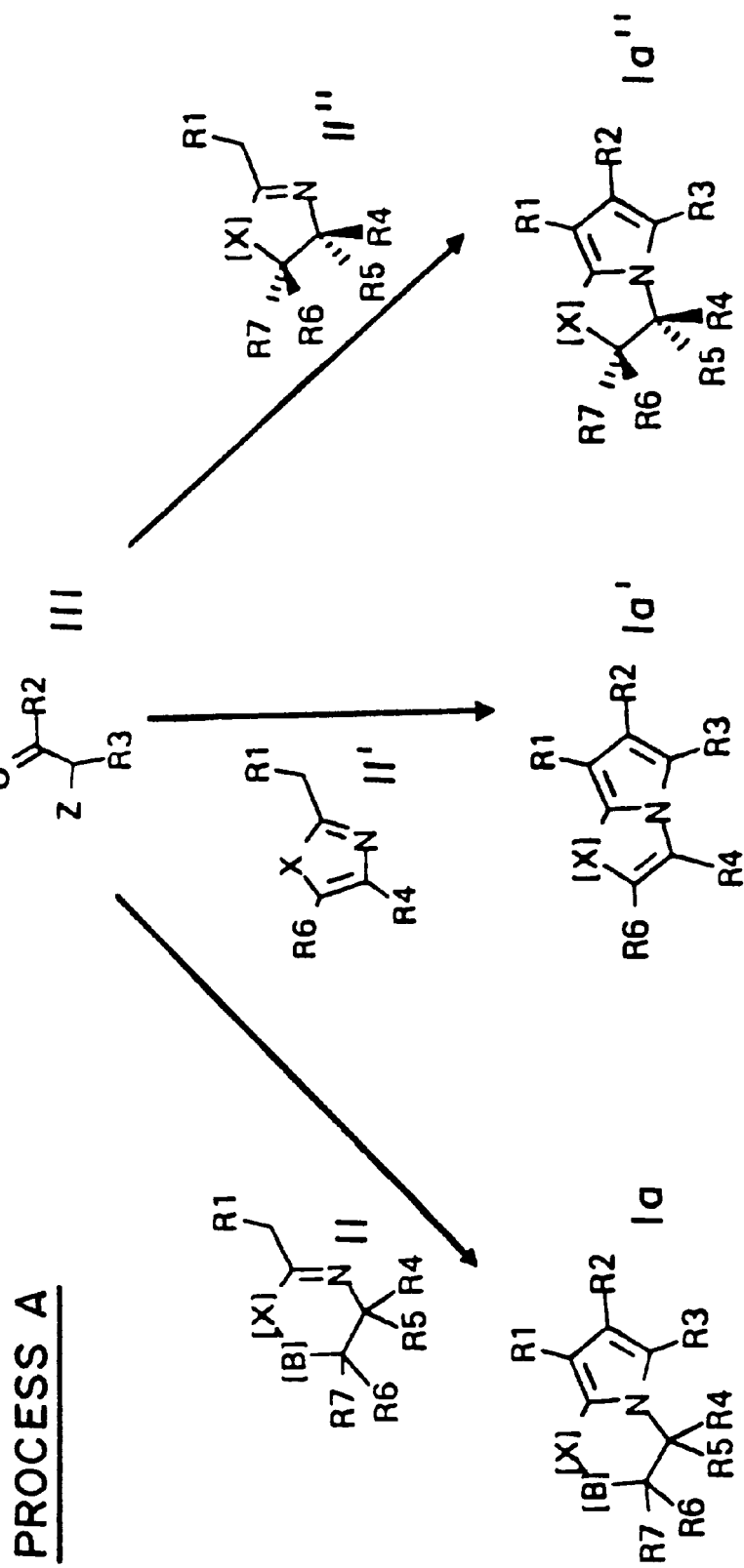
Figure 1B:
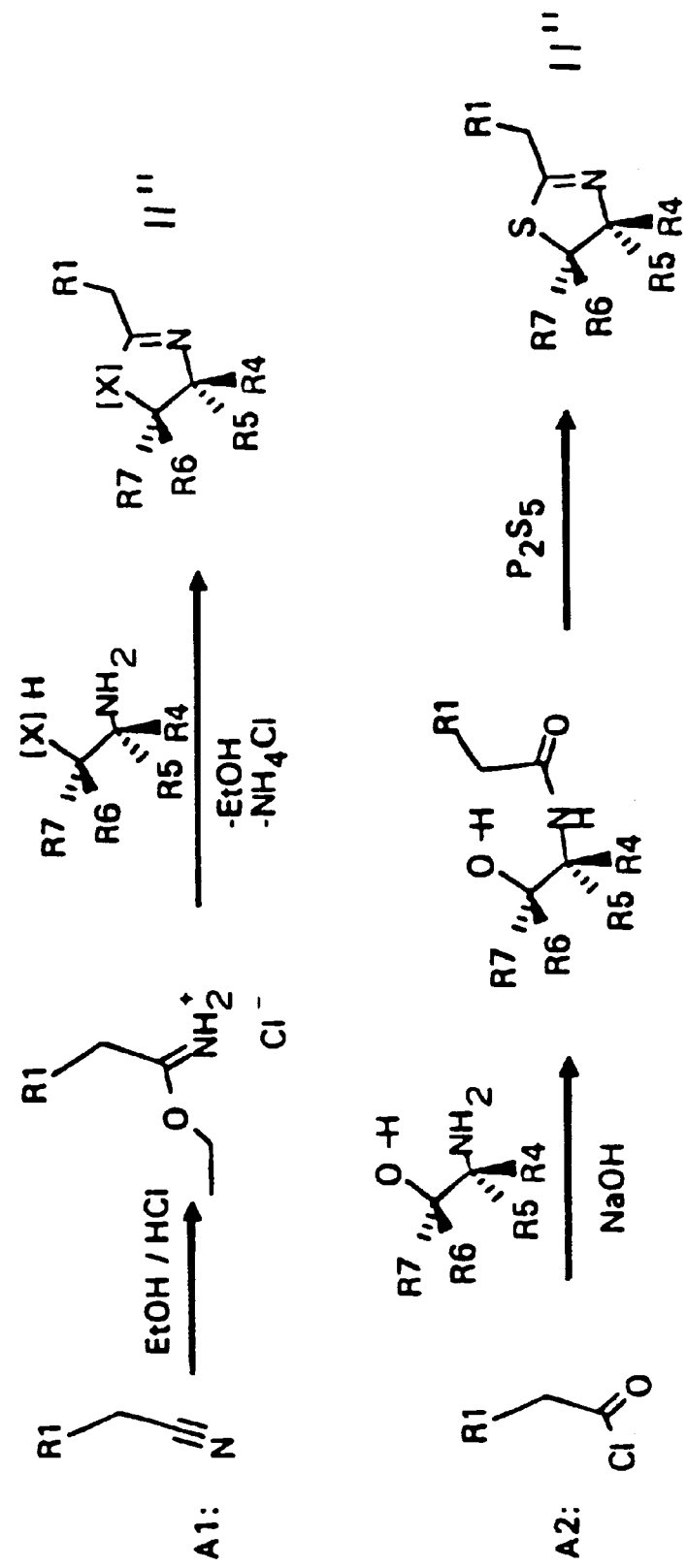
Figure 1C:
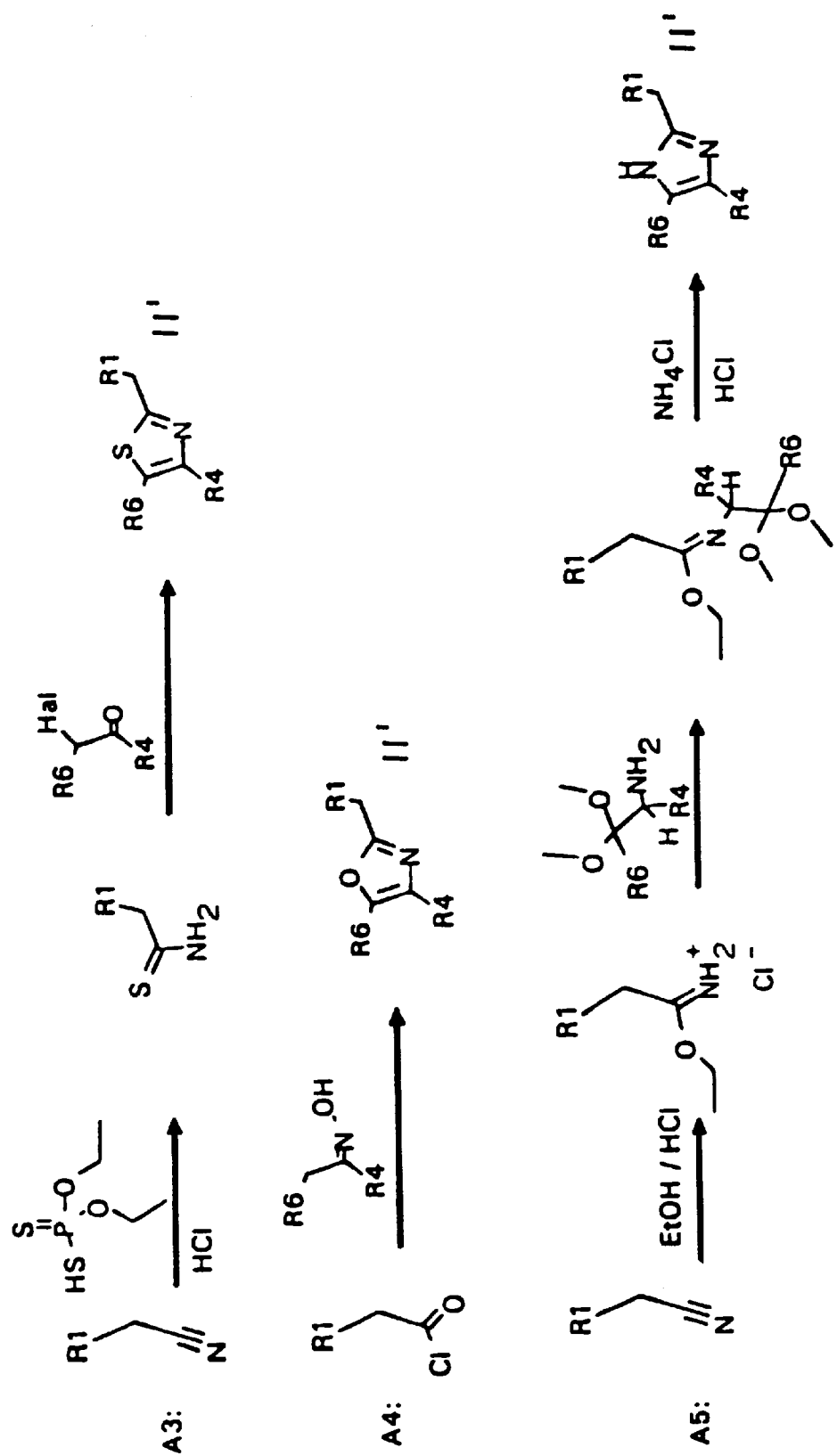
Figure 2:
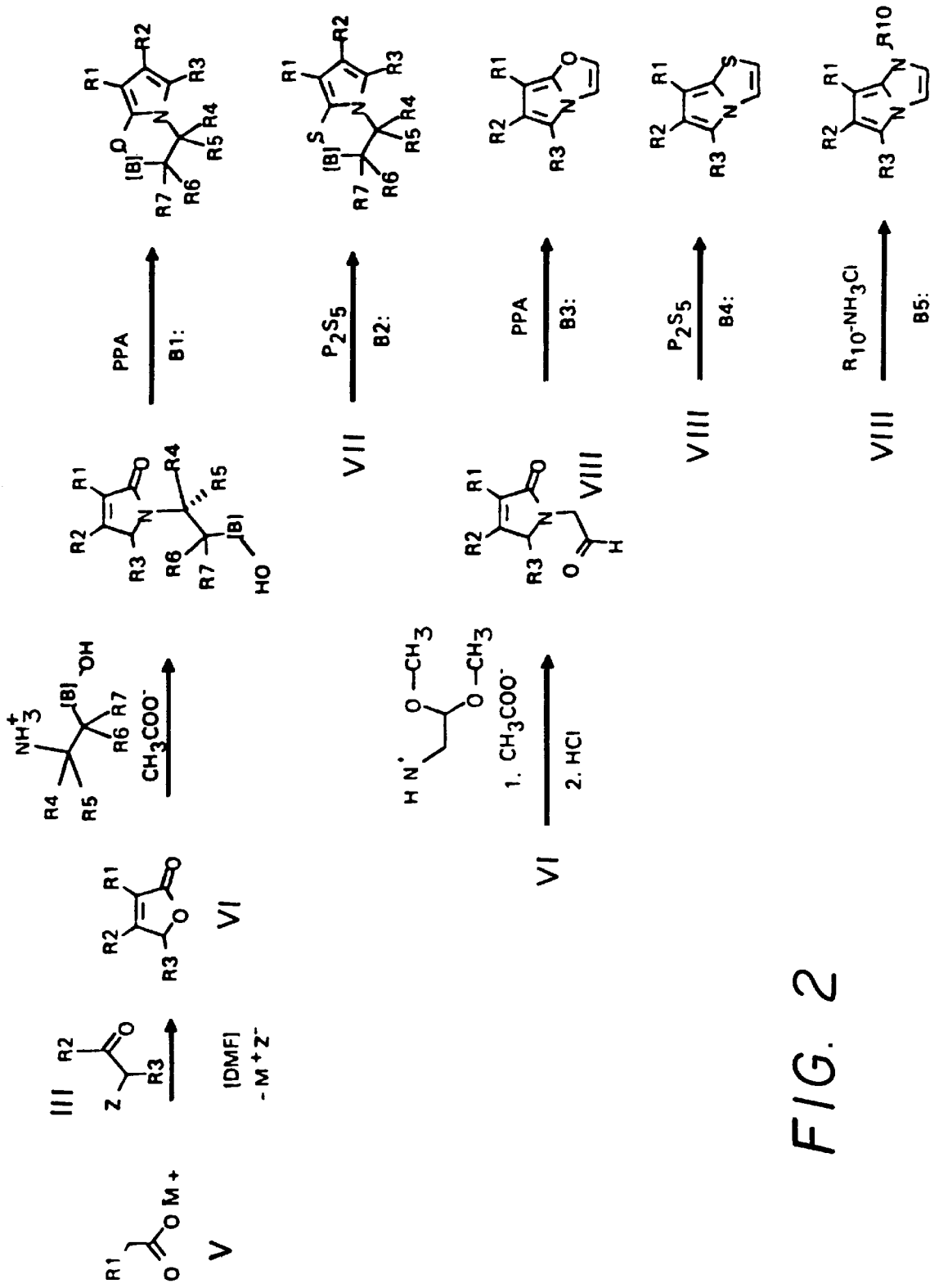

Depending on the condensation reagent used and on the second functional group of the bifunctional amines $NH_2$—$CR^4R^5CR^6R^7$—$[B]_a$—OH or $NH_2CH_2CH(OCH_3)_2$, the cyclization to the anellated heterocycle leads to partially hydrated forms (formula I'', FIG. 2: B1/B2) or to dehydrated forms (formula I', FIG. 2: B3, B4, B5).

Figure 3A:
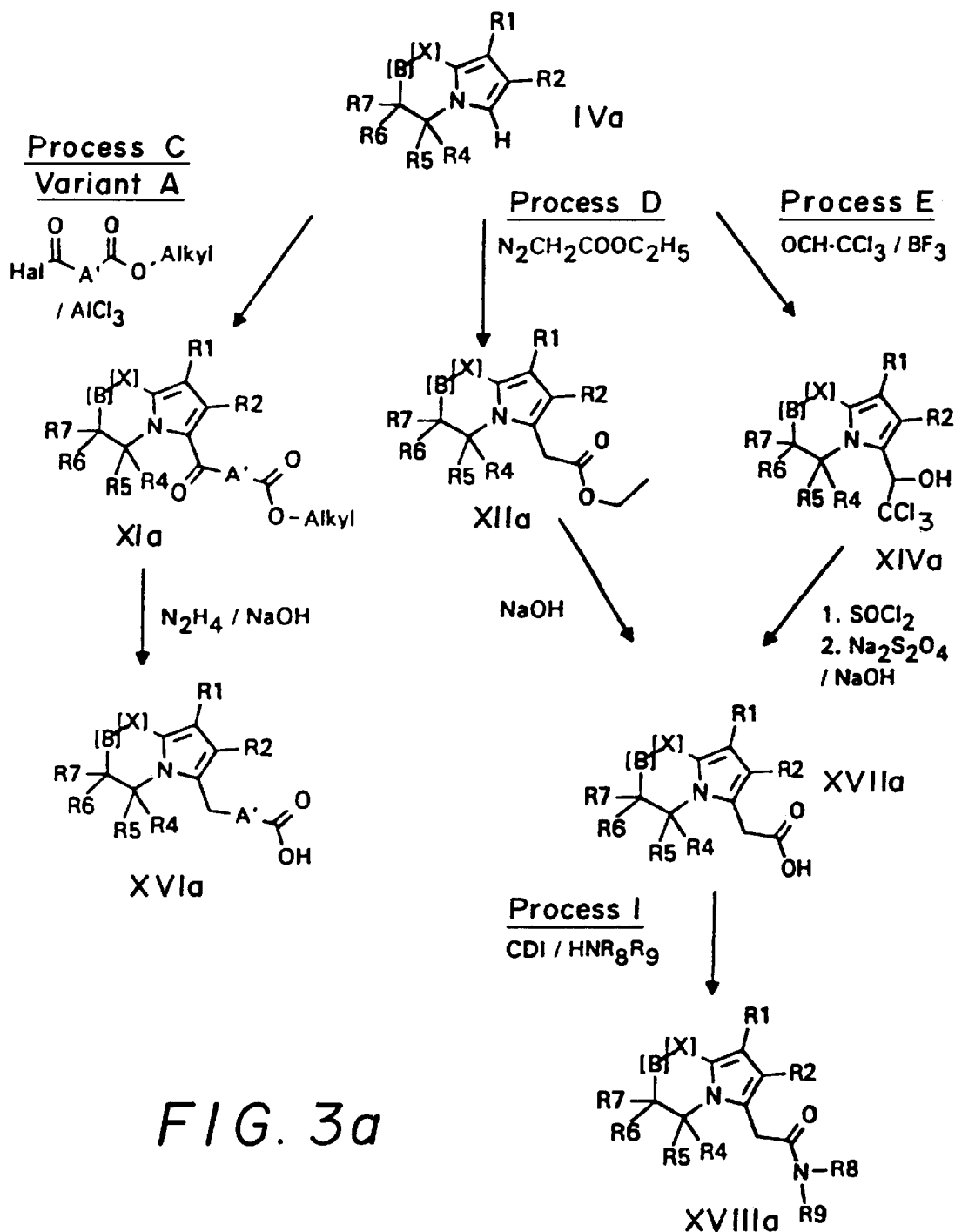

If so desired, a different substituent is inserted into the heterocyclic base structure, according to methods known to one skilled in the art. For example, these methods can include:

a) Reaction of a formula IV compound with a carboxylic acid halogenide HalOC—A'—COO alkyl, in which A' stands for a chemical bond, $C_1$–$C_7$ alkylene or $C_2$–$C_7$ alkenylene and Hal stands for Cl or Br (FIG. 3a, process C/variant A). The formula Ia compound obtained, in which one of the radicals $R^1$, $R^2$, and $R^3$ stands for CO—A'—$CO_2$ alkyl, is then treated with a reagent which is suitable for the reduction of the carbonyl group to a $CH_2$ group, for example hydrazine, $NaCNBH_3$ or zink amalgam. The reaction with the carboxylic acid halogenide is carried out in an inert solvent, e.g. diethyl ether or tetrahydrofuran, optionally in the presence of a catalyst. The reduction with hydrazine is preferably carried out in a high-boiling alcohol, e.g. diethylene glycol. The formula XVI compounds are obtained in this manner.

b) The production of the formula Ia compounds, in which one of the radicals $R^1$, $R^2$, and $R^3$ stands for A—$CONR^8R^9$, is carried out starting from the correspondingly activated derivatives of formula Ia carboxylic acid, in which one of the radicals $R^1$, $R^2$, or $R^3$ stands for $ACO_2H$, by means of reaction with the corresponding sulfonamide, hydroxyl amine, amine, or amide (see FIG. 3a, formula XVIII, A=$CH_2$). Suitable activated carboxylic acid derivatives are known to one skilled in the art, the imidazolide derivative is preferable.

Figure 3B:
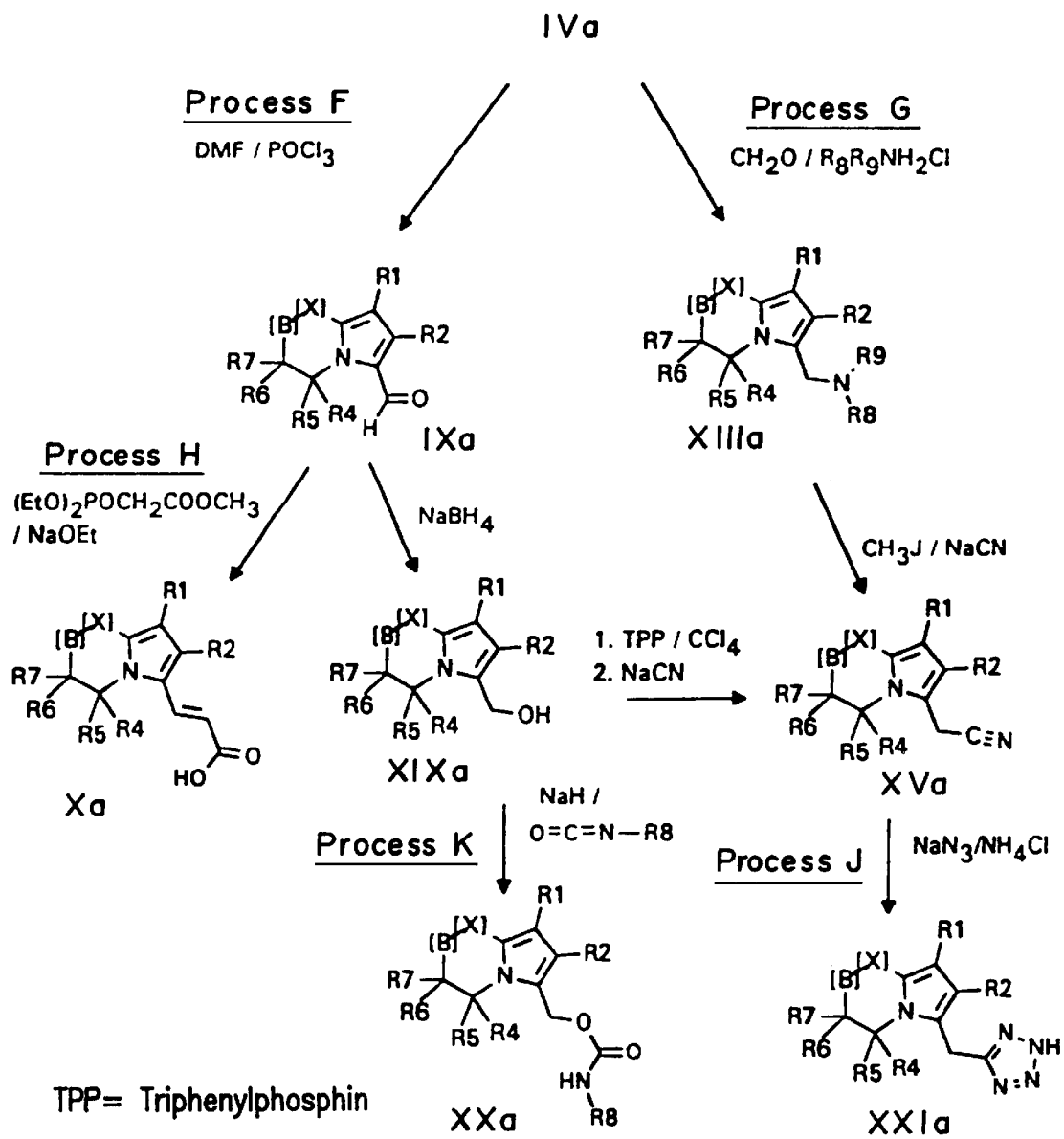
Figure 4:
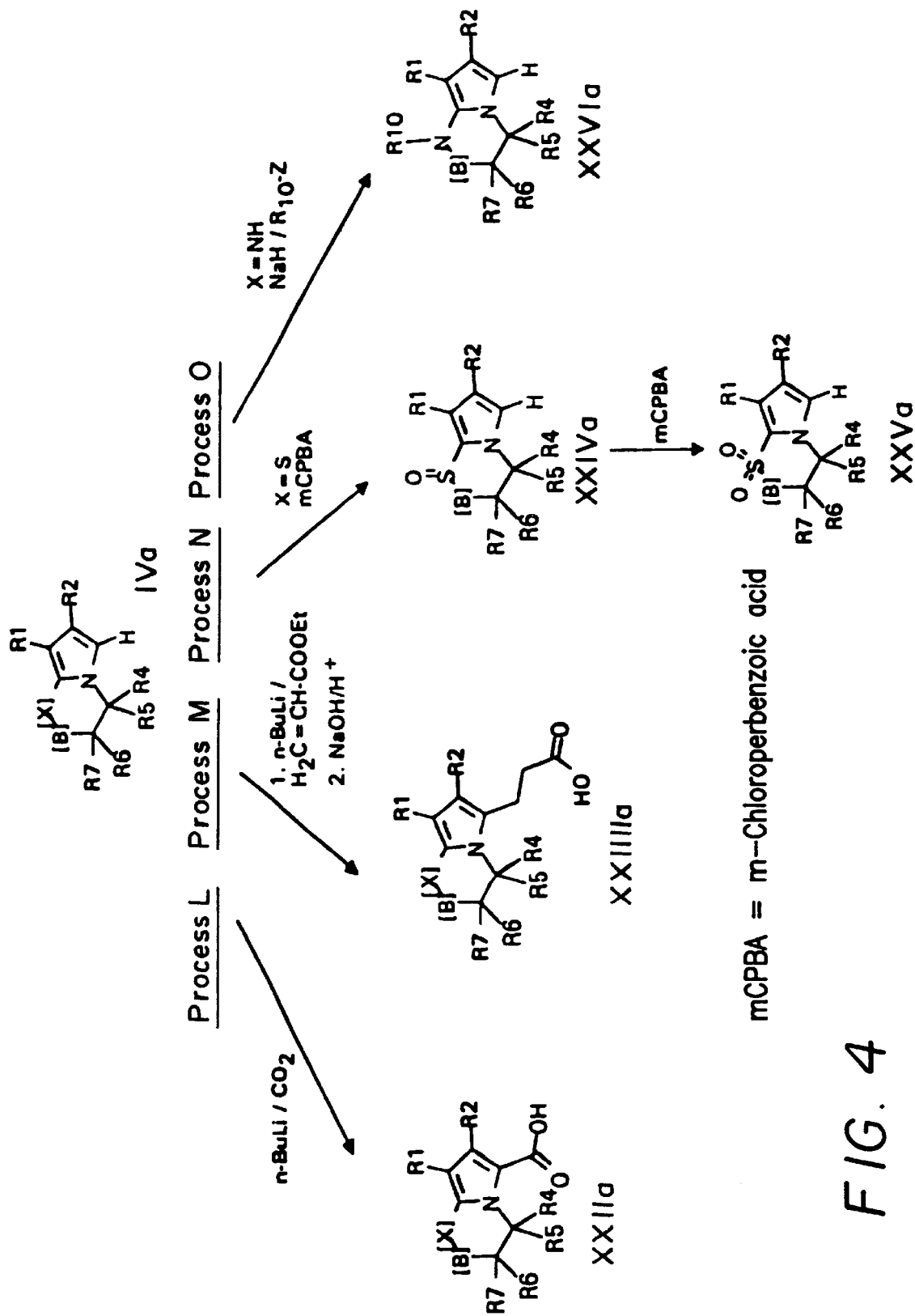

The reaction is carried out in an inert solvent, for example an ether such as diethyl ether or tetrahydrofuran, in the presence of a base, for example sodium hydride. The reaction temperature lies in the range that extends from room temperature to the boiling point of the solvent. The reaction is suitably carried out at room temperature.

c) There are a number of methods available for inserting the particularly preferable group $CH_2CO_2H$ (see FIGS. 3a, 3b, and 4). The first possibility is comprised in that a formula IV compound is reacted with oxalyl chloride (FIG. 5b), wherein a formula I compound is obtained, in which one of the radicals $R^1$, $R^2$, and $R^3$ stands for $COCO_2H$. This compound is then treated with a reagent which is suited to the reduction of the ketocarbonyl group, for example hydrazine, $HaCNBH_3$, or zinc amalgam. The reduction with hydrazine is preferable under the conditions of a Wolff-Kishner reduction and in particular the Huang-Minlon variant of it (also see point a) above).

Another possibility is comprised in reacting a formula IV compound with a diazoethanoic acid alkyl ester producing a formula I compound in which one of the radicals $R^1$, $R^2$, and $R^3$ stands for $CH_2COO$ alkyl. If so desired, this compound is then subjected to an ester cleavage into the corresponding free carboxylic acid. (FIG. 3a, XVII).

The reaction with the diazoethanoic acid is carried out in an inert solvent, for example toluene or xylene, in the presence of copper powder or complex copper(I) salts or copper(II) salts. The reaction is carried out at an increased temperature, suitably at the boiling temperature of the solvent used.

A further possibility is comprised in the reaction of a formula IV compound with chloral producing a formula XIV compound and treatment of the activated compound with a dithionite, for example sodium dithionite or with a sulfinate, e.g. hydroxymethane sulfinic acid sodium salt.

d) The insertion of a formyl group or methylol group into the pyrrole ring is carried out through the reaction of a formula IV compound with phosphorus oxychloride/dimethyl formamide (see FIG. 3b). The reaction is carried out in an inert solvent, for example benzene, toluene, or xylene, at an increased temperature, suitably at the boiling point of the solvent used. A formula IX compound is obtained, in which one of the radicals $R^1$, $R^2$, and $R^3$ stands for CHO. This formyl group can then be reduced in a usual way, for example with lithium aluminum hydride in an inert solvent, for example tetrahydrofuran, or with sodium hydroboron in aqueous alkaline solution, forming the corresponding hydroxymethyl compound XIX (FIG. 3b). This can then be used as a starting material for further reactions for the insertion of the desired groups (process K, J; FIG. 3b).

Furthermore, the formyl group in a Wittig reaction carried out under normal conditions can be transformed into a corresponding alkenylene group producing the compound X (see compound X in FIG. 3b). If so desired, this can in turn be hydrated in a usual way, forming the corresponding alkylene compound (XXIII, FIG. 4).

e) Reaction of a formula IV compound with an anhydride with the formula:

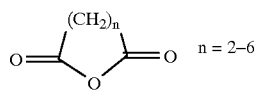

produces the corresponding formula I ketocarboxylic acids, in which one of the radicals $R^1$, $R^2$, and $R^3$ stands for $CO(CH_2)_aCO_2H$. With the reagent already mentioned, the ketocarbonyl group can be reduced to a $CH_2$ group (see FIGS. 3, 3a, XI–XVI).

f) A carboxyl group can be inserted by the reaction of a formula IV compound with n-butyl lithium in an inert solvent at a low temperature and by the subsequent routing of $CO_2$ gas through the solution of the lithium organic compound formed; formula XXII compounds are obtained (see process L, FIG. 4).

g) Esters can be produced from carboxylic acids in a customary fashion by esterifying and carboxylic acids can be produced from esters in a normal manner by ester cleavage.

The production of other compounds according to the invention is carried out analogously (FIGS. 3a, 3b, 4), optionally through further reactions which are known to one skilled in the art.

The compounds according to the invention have proven to be potent cyclooxygenase and/or lipoxygenase inhibitors. They can therefore be used in the treatment of diseases which are associated with a change of the arachidonic acid metabolism. In particular, this pertains to diseases of the rheumatoid variety and the prevention of allergically induced diseases. The compounds according to the invention consequently represent effective anti-inflammatory drugs, analgesics, antipyretics, antiallergics, and broncholytics and are effective against bronchial constriction and can therefore be used for thrombosis prophylaxis and for the prophylaxis of anaphylactic shock as well as for the treatment of dermatological diseases such as psoriasis, urticaria, acute and chronic exanthemas of allergic and non-allergic genesis.

The compounds according to the invention can be administered either as individual therapeutic agents or as mixtures with other therapeutic agents: they can be administered as is, but in general, they are administered in the form of pharmaceutical agents, that is, as mixtures of agents with suitable pharmaceutical vehicles or diluents. The compounds or agents can be administered orally or parenterally, preferably, though, they are given in oral dosage forms.

The type of pharmaceutical agent and of the pharmaceutical vehicle or diluent depends on the desired administration type. Oral agents can be in tablet or capsule form and can contain conventional excipients such as binders (e.g. syrup, acacia, gelatine, sorbitol, tragacanth, or polyvinyl pyrrolidone), fillers (e.g. lactose, sugar, cornstarch, calcium phosphate, sorbitol, or glycine), lubricants (e.g. magnesium stearate, talcum, polyethylene glycol, or silicon dioxide), disintegrating agents (e.g. starch), or wetting agents (e.g. sodium lauryl sulfate). Oral fluid preparations can be in the form of aqueous or oleaginous suspensions, solutions, emulsions, syrups, elixirs, or sprays, etc. or can be in the form of dry powder for reconstitution in water or another suitable vehicle. Fluid preparations of this kind can contain conventional additives, for example suspension agents, flavorings, diluents, or emulsifying agents. For parenteral administration, solutions or suspensions can be used with standard pharmaceutical vehicles.

The compounds or agents according to the invention can be administered to a mammal (human and animal) in doses of approximately 0.5 mg to approximately 100 mg per kg of body weight per day. They can be administered in a single dose or in a number of doses.

The efficacy of the compounds according to the invention can be determined from the inhibition of 5-lipoxygenase or cyclooxygenase. Experiments have be carried out according to Dannhardt et al., J. Pharm. Pharmacol. 1992, 44: 419–424. It has been discovered that the compound of example 1 (X=N—Ph) inhibits 5-lipoxygenase to 95% at 1 $\mu$mol/l, while the corresponding compound of the prior art (X=$CH_2$) demonstrates only a slight inhibiting effect.

The following examples explain the invention. All temperature data is uncorrected. The IR spectra of crystalline substances were picked up from a KBr compact, the oily substances from a film. Unless otherwise noted, the NMR spectra are 200 MHz spectra, recorded in $CDCl_3$ with tetramethyl silane (TMS) as an internal standard. The IR spectra are indicated in $cm^{-1}$ and the NMR spectra are indicated in $\delta$(ppm).

EXAMPLE 1

4,6,7-triphenyl-2,3-dihydro-Pyrrolo-[2,1-b]-imidazole ethanoic acid

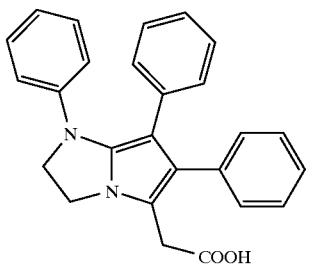

A) 2-benzyl-N-phenylimidazoline 0.88 mol HCl gas was dissolved at −20° C. in 65 ml of 100% pure ethanol. 0.8 mol benzyl cyanide was then dropped in with cooling so that the internal temperature did not exceed 15° C. After 2 hours of stirring at 15–20° C., a solution of 0.76 mol ammonia gas was dropped into 160 ml of ethanol, where attention was paid that the temperature did not exceed 20° C. Then 0.8 mol N-phenylethylene diamine was dropped in. After an hour of stirring at room temperature, the ethanol was distilled off up to a residue temperature of 110° C. After cooling, 250 ml water was added, the mixture was made alkaline with NaOH, and was multiply extracted using methylene chloride. The residue remaining after the evaporation of the dried organic phases was fractionally distilled. The desired product crosses over at 135–145° C./0.5 mbar.

Yield 35%.

IR spectrum: 3270, 3055, 2930, 1621, 1613, 1490, 1385, 1312, 1255, 1178, 1025, 754, 734, 715 cm$^{-1}$.

$^1$H-NMR spectrum (200 MHz): 7.3–6.9 (m, 1H, arom.), 3.86–3.77 (m, 4H, (N—CH$_2$—CH$_2$—N), 3.63 (s, 2H, —CH$_2$—Ph).

B) 4,6,7-triphenyl-2,3-dihydro-pyrrolo-[2,1-b]imidazole

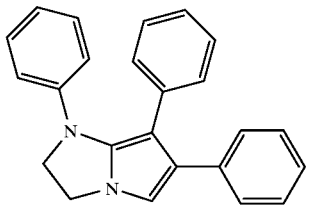

48 mmol 2-benzyl-1-phenyl-Δ-2-imidazoline, which was dissolved in 60 ml diethyl ether, was dropped, while stirring, into a solution of 48 mmol phenacyl bromide in 60 ml dry diethyl ether. After the addition was terminated, stirring continued for another hour and then the solution was left standing overnight. The suspension was carefully decanted and the precipitate was absorbed in 250 ml dry methylene chloride and 160 ml diethyl ether was added. Then 48 ml dry triethyl amine was dropped in while stirring. After the addition was terminated, stirring continued for six more hours at room temperature. The volatile components were evaporated at a reduced pressure and the remaining residue was purified using acid chromatography (silica gel, solvent THF). The oily product was brought to crystallization with diethyl ether.

Yield: 48%.
Melting point: 172° C.

IR spectrum: 1596, 1555, 1493, 1430, 1393, 1315, 1100, 1019, 757, 697.

1H-NMR spectrum (200 MHz): 7.48–6.67 (m, 15H, arom), 6.59 (s, 1H, —CH═C), 4.45 (t, 2H, J=10 Hz), 4.19 (t, 2H, J=10 Hz).

C) 4,6,7-triphenyl-2,3-dihydro-pyrrolo-[2,1-b]-imidazole]-5-yl-ethanoic acid ethyl ester

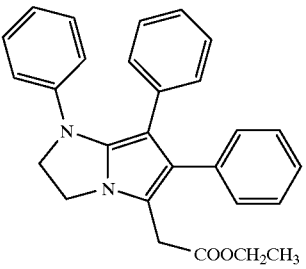

10 mmol of the product from step B was dissolved in 80 ml dry toluene and 0.6 g copper powder and 40 mmol diazoethanoic ester were added. The mixture was heated with recycling for one hour. After the copper powder was filtered out and the solvent was withdrawn, the residue was purified using acid chromatography (neutral aluminum oxide, solvent n-hexane/isopropyl ether). The product was recrystallized from isopropanol.

Yield: 31%.
Melting point: 116° C.
IR spectrum: 1723, 1598, 1559, 1495, 1435, 1190, 1026, 748, 694.

$^1$H-NMR spectrum: 7.31–6.54 (m, 15H, arom); 4.43 (t, 2H, J=7.3 Hz); 4.19 (t, 2H, J=7.3), 4.20 (q, 2H, J=7.2, ethyl); 3.55 (s, 2H, —CH$_2$— C=0); 1.30 (t, 3H, J=7.2 ethyl).

D) 4,6,7-triphenyl-2,3,-dihydro-pyrrolo[2,1-b]-imidazole-5-yl-ethanoic acid

The ester compound from step C was dissolved in methanol and stirred for one hour with a 10% molar excess of finely powdered sodium carbonate. The filtrate obtained after the solids were filtered out was evaporated and the residue was washed with isopropyl ether, where 89% of the title compound was obtained in the form of sodium salt, from which the free acid can be obtained by acidifying if so desired.

Melting point: 181° C.
IR-spectrum: 1704 (C═O).
$^1$H-NMR spectrum: 7.30–6.48 (m, 15H, ar.); 4.42 (t, 2H, J=7.3 Hz); 4.21 (t, 2H, J=7.3 Hz); 3.48 (s, 2H, CH$_2$).

EXAMPLE 2

{[3-methyl-6-(4-chlorophenyl)-7-phenyl1pyrrolo-[2,1-b]-thiazole-5-yl}ethanoic acid

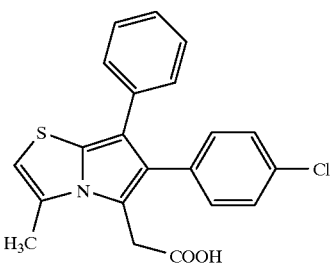

A) 2-benzyl-4-methyl thiazole 15 g thiophenyl acetamide (0.1 mol) was suspended in 200 ml toluene and the toluene suspension was heated with recycling. 13.9 g chloracetone (0.15 mol) was dropped into the solution produced and then the mixture was heated for another hour with recycling. After cooling in an ice bath, the precipitate was decanted off. The thiazole was freed from the hydrochloride with sodium dicarbonate solution and absorbed in isopropyl ether. The aqueous solution was multiply extracted with isopropyl ether. The isopropyl ether phase was dried via sodium sulfate and evaporated and the oily residue was fractionally distilled. The yield was 14 g (74% of the title compound). For further reaction, the residue obtained after the evaporation of the isopropyl ether can be used directly without distillation.

$^1$H-NMR spectrum: 2.426 (d; J=0.8 Hz, 3H); 4.29 (s; 2H) 6.725 (q, J=0.8 Hz, 1H) 7.0–7.5 (5H, m).

B) 6-(4-chlorophenyl)-3-methyl-7-phenyl-pyrrolo-[2,1-b]thiazole

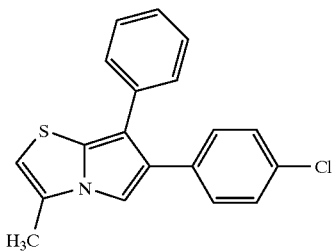

(1) 9.4 g 2-benzyl-4-methyl thiazole (0.05 mol) and 11.6 g ω-bromine-4-chloracetophenone (0.05 mol) were heated to 80° C. for 2 hours in a water bath, wherein after an initial liquefaction of the mixture, a solid was formed once more. The hardened mass was comminuted and removed using chloroform irrigation. The crystalline solid was aspirated, washed with chloroform, and subsequently dried.

Yield: 13.6 g (66%).

(2) 13 g of the thiazolium salt obtained according to (1) was heated with 3.8 g triethyl amine in 200 ml chloroform for 2 hours with recycling. After cooling, the mixture was filtered and the filtrate was extracted 2 times with 200 ml water. The chloroform phase was then dried and evaporated. 8.2 g (67%) of the title compound was obtained as a leathery mass.

$^1$H-NMR spectrum: 2.395 (d, 3H, J=0.8 Hz); 6.308 (q, 1H, J=0.8 Hz); 7.16 (s, 1H); 7.1–7.4 (m; 9H; ar2).

C) 2-[6-(4-chlorophenyl)-3-methyl-7-phenyl-pyrrolo-[2,1-b]-thiazole-5-yl]-2-oxo-ethanoic acid ethyl ester

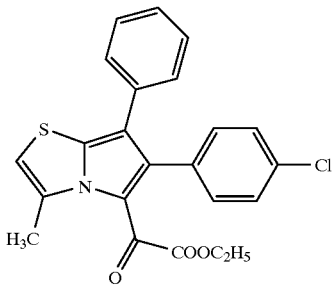

0.75 g of the product (2.3 mmol) obtained according to (B) was dissolved in 10 ml methylene chloride and then 0.31 g oxalic acid ethyl ester acid chloride in 2 ml methylene chloride was dropped into this solution at room temperature. Then the mixture was stirred for another hour, 5 ml water was added, and the methylene chloride phase was then separated out, dried via sodium sulfate, and evaporated in the vacuum. 0.6 g of the title compound was obtained, with a melting point of >200° C. (decomposition).

IR spectrum: 1725, 1711.

$^1$H-NMR spectrum: 1.1 (t, 3H, J=7 Hz, CH$_3$); 2.71 (d, 3H, J=0.8 Hz); 3.72 (q, 2H, CH$_2$, J=7 Hz); 6.3 (q, 1H, J=0.8 Hz); 7.07 7.41 (m, 9H, ar.).

D) 2-[6-(4-chlorophenyl)-3-methyl-7-phenyl-pyrrolo-[2,1-b]-thiazole-5-yl]-ethanoic acid

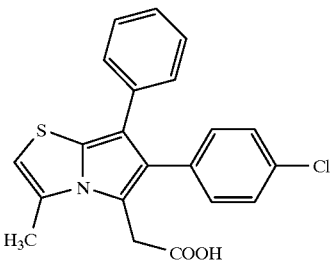

The title compound was produced according to the general working instructions in European Patent Disclosure EP-A-397 175 for producing 4-(diphenyl-2,3-dihydro-1H-pyrolizinyl)butyric acids from the corresponding 4-oxobutyric acids by means of reduction with hydrazine. The title compound was obtained at a yield of 73% and with a melting point of 194–196° C. (decomposition).

IR spectrum: 3430, 1710, 1595, 1518, 1396, 1222, 1088, 1011, 841, 711 cm$^{-1}$.

$^1$H-NMR spectrum: 7.3–7.03 (m, 9H, arom.); 6.325–6.320 (d, 1H, J=0.8 Hz); 3.76 (s, —CH$_2$—, 2H); 2.569–2.566 (d, 2H, J=0.8 Hz).

EXAMPLE 3

{[6-(4-chlorophenyl)-3-methyl]-pyrrolo-[2,1-b]-thiazole-5yl}-ethanoic acid

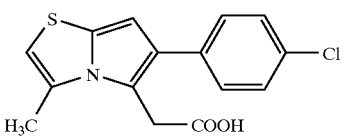

A) 3-Methyl-6-(4-chlorophenyl)-pyrrolo-[2,1-b]-thiazole

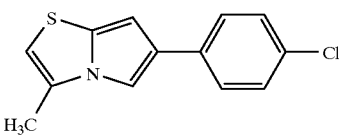

The production was carried out analogous to step (B) of example 2. The title compound was obtained at a yield of 53% and with a melting point of 116° C.

$^1$H-NMR spectrum: 2.365 (3H, d, J=0.8 Hz, CH$_3$), 6.262 (q, 1H, 0.8 Hz), 6.480 (d, 1H, J=1.6 Hz), 7.289 (d, 1H, J=1.6 Hz) 7.3–7.6 (AA'BB', 4H).

B) 6-(4-chlorophenyl)-3-methyl-pyrrolo-[2,1-b]-thiazole-5-yl-ethanoic acid-ethyl ester-3-methyl

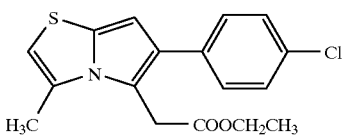

1.2 g of the compound (0.005 mol) obtained according to step (A) was dissolved in 20 ml toluene under heat and 0.5 g copper powder was added. 2.3 g (20 mmol) diazoethanoic ester was added in small portions and the reaction mixture was heated with recycling for 8 more hours. The copper powder was filtered out, the filtrate was evaporated until dry, and the residue was purified using acid chromatography. 0.8 g of the title compound was obtained as oil.

IR spectrum: 1728 (C=O).

$^1$H-NMR spectrum: 1.12 (t, 3H, CH$_3$, J=6.7 Hz); 2.62 (d, 3H, J=0.8 Hz, CH$_3$); 3.58 (q, 2H, CH$_2$, J=6.7), 6.35 (s, 1H); 6.58 (q, 1H, J=0.8 Hz); 7.18–7.41 (AA'BB', ar.).

C) 6-(4-chlorophenyl)-3-methyl-pyrrolo-[2.1-b-]thiazole-5-yl-2-oxo-ethanoic acid-ethyl ester

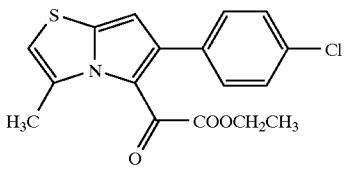

The synthesis is carried out analogous to step (C) of example 2. 67% of the title compound was obtained with a melting point of >200° C. (decomposition).

IR spectrum: 1732, 1617.

$^1$H-NMR spectrum: 1.087 (t, 3H, CH$_3$) 2.698 (d, 3h, J=0.8 Hz); 3.664 (q, 2H, CH$_2$), 6.37 (1H, s), J=6.7 Hz, 6.523 (q, 1H, J=0.8 Hz); 7.20–7.40 (AA'BB', 4H).

D) {6-(4-chlorophenyl)-3-methyl]-pyrrolo-[2.1-b]thiazole-5yl}-ethanoic acid

The synthesis was carried out analagous to step (D) of example 2. 81% of the title compound was obtained with a melting point >190° C. (decomposition).

IR spectrum: 1690 cm$^{-1}$ (C=O).

$^1$H-NMR spectrum: 2.52 (d, 3H, CH$_3$); 4.00 (s, 2H, CH$_2$); 6.15 q, (q, 1H, =CH), 6.21 (s, 1H, =CH), 7.25–7.5 (m, 4H, ar).

EXAMPLE 4

2-[6-(4-chlorophenyl)-2,3-dimethyl-7-phenyl-pyrrolo[2,1-b]thiazole-5-yl]-ethanoic acid According to Process A3

A) 2-benzyl-4,5-dimethyl-thiazole analogous to example 2, letter A 3-bromine-2-butanone is dropped into the hot solution of phenylthioacetamide (3.75 g, 0.025 mol) in toluene (40 mL) and recycled for 2 more hours. After cooling of the toluene, the residue decanted is dissolved in chloroform (50 mL) and neutralized with Na$_2$CO$_3$ solution (20 mL, 10%), the chloroform phase is dried (Na$_2$SO$_4$), reduced in the vacuum, and the remaining brownish-yellow residue is distilled: yellow oil, boiling point 98–100° C. (5·10$^{-1}$).

C$_{12}$H$_{13}$NS (MG=203.3).

IR (cm$^{-1}$): 2915, 1599, 1551, 1488, 1449, 1424, 1122, 1026, 755, 702.

$^1$H-NMR (200 MHz, CDCl$_3$): 7.40–7.10 (m, 5H, arom.), 4.208 (s, 2H, CH$_2$), 2.294 (s, 3H, CH$_3$), 2.258 (s, 3H, CH$_3$).

B) 2-benzyl-3-[2-(4-chlorophenyl)-2-oxo-ethyl]-4,5-dimethyl thiazolium bromide

C$_{20}$H$_{19}$BrClNOS (MG=436.8).

Leathery mass of CHCl$_3$, substance not isolated, but transformed further as a raw product.

C) 6-(4-chlorophenyl)-2,3-dimethyl-7-phenyl-pyrrolo[2,1-b]thiazole

C$_{20}$H$_{16}$ClNS (MG=337.87).

IR (cm$^{-1}$): 1594, 1514, 1411, 1088, 831, 756, 696.

$^1$H-NMR (200 MHz, CDCl$_3$): 7.35–7.10 (m, 5H, arom.), 7.07 (s, 1H, pyrr.), 2.31 (s, 3H, CH$_3$), 2.29 (s, 3H, CH$_3$).

D) 2-[6-(4-chlorophenyl)-2,3-dimethyl-7-phenylpyrrolo[2,1-b]thiazole-5yl]-2-oxo-ethanoic acid-ethyl ester C$_{24}$H$_{20}$ClNO$_3$S (437.9).

Melting point: 167° C.

IR (cm$^{-1}$): 1724, 1623, 1396, 1274, 1244, 1020, 750, 694.

$^1$H-NMR (200 MHz, CDCl$_3$): 7.40–7.05 (m, 9H, 2 arom.), 3.635 (q, 2H, J=7.1 Hz, CH$_2$), 2.564 (q, 3H, J=0.6 Hz, CH$_3$), 2.393 (q, 3H, J=0.6 Hz, CH$_3$); 1.10 (t, J=7.1 Hz, CH$_3$).

E) 2-[6-(4-chlorophenyl)-2,3-dimethyl-7-phenylpyrrolo[2,1-b]thiazole-5-yl]-ethanoic acid C$_{22}$H$_{18}$ClNO$_2$S (MG=395.9)

Melting point: 166° C.

IR (cm$^{-1}$): 3425, 3070, 2950, 1710, 1596, 1517, 1482, 1394, 1214, 1008, 1010, 840.

$^1$H-NMR (200 MHz, CDCl$_3$): 7.40–7.05 (m, 9H, 2 arom.), 3.92 (s, 2H, CH$_2$), 2.448 (s, 3H, CH$_3$), 2.297 (s, 3H, CH$_3$).

EXAMPLE 5

2-[6-(5-chloro-2-thienyl)-3-methyl-7-phenyl-pyrrolo[2,1-b]thiazole-5-yl]-ethanoic acid According to Process A3

A) 2-benzyl-3-[2-(4-chlorothienyl)-2-oxo-ethyl]-4-methyl-thiazolium bromide

From 2-benzyl-4-methyl-thiazole and 2-bromine-1-(5-chloro-2-thienyl)-ethanone, analogous to example 2, letter A C$_{17}$H$_{15}$BrClNOS$_2$ (MG=428.8).

$^1$H-NMR (200 MHz, DMSO-d6): 7.91 (d, 1H, J=4.2 Hz, thien.), 7.56 (s, 1H, thiaz.), 7.00 (s, 5H, arom.), 6.88 (d, 1H, J=4.2 Hz, thien.), 6.101 (s, 2H, CH$_2$CO), 4.369 (s, 2H, —CH$_2$Ph), 2.155 (s, 3H, CH$_3$).

B) 6-(5-chloro-2-thienyl)-3-methyl-7-phenyl-pyrrolo[2,1-b]thiazole

C$_{17}$H$_{12}$ClNS$_2$ (MG=329.87).

IR (cm$^{-1}$): 1591, 1522, 1395, 1160, 791, 762, 719, 694, 624.

$^1$H-NMR (200 MHz, CDCl$_3$): 7.43–7.16 (m, 6H, arom.+pyrr.), 6.782 (d, 1H, J=3.8 Hz, thien.), 6.658 (d, 1H, J=3.8 Hz, thien.), 6.302 (s, 1H, thiaz., J=1.25 Hz,), 2.374 (q, 3H, J=1.25 Hz, CH$_3$).

C) 2-[6-(5-chloro-2-thienyl)-3-methyl-7-phenyl-pyrrolo[2,1-b]thiazole-5-yl]-2-oxo-ethanoic acid chloride, (variant B)

Oxalylchloride (22.5 g, 0.2 mol) is dropped with ice cooling into the solution of 6-(5-chloro-2-thienyl)-3-methyl-7-phenyl-pyrrolo[2,1-b]thiazole (49.3 g, 0.15 mol) in THF (300 mL), the mixture is stirred at room temperature for another 15 minutes and water is carefully added (20 mL).

The acid chloride produced is not isolated, but as a raw product is reacted further with hydrazine hydrate/KOK in diethylene glycol:

D) 2-[6-(5-chloro-2-thienyl)-3-methyl-7-phenylpyrrolo[2,1-b]thiazole-5-yl]-ethanoic acid Hydrazine hydrate (75 mL) is added with ice cooling to the aqueous THF phase obtained in letter C) and then THF is distilled out in the vacuum. Diethylene glycol (120 mL)

is added to the cooled residue and KOH (120 g) is added. The mixture is slowly heated to 140° C. and kept at this temperature until only slight water residues are still crossing over to the water separator and the foam buildup reduces. The hot reaction mixture is poured onto ice (1 L) and acidified with HCl (pH=2). Separated carboxylic acid is rapidly absorbed with diethyl ether (1 L). The ether phase is dried via $Na_2SO_4$ and reduced at a lowered pressure. The solution of the solidified residue kept in the heat is cooled in toluene to crystallize the carboxylic acid: 17 g (29%) cream-colored cristals with a melting point of 182–183° C.

$C_{19}H_{14}ClNO_2S_2$ (MG=387.91).

IR($cm^{-1}$): 3425, 1694, 1596.

$^1$H-NMR (200 MHz, $CDCl_3$): 7.40–7.1 (m, 5H, arom.), 6.871 (d, 1H, J=4.0 Hz, thien.), 6.731 (d, 1H, J=4.0 Hz, thien.), 6.306 (s, 1H, thiaz., J=1.0 Hz,), 4.043 (s, 2H, $CH_2$), 2.554 (q, 3H, J=1.0 Hz, $CH_3$).

EXAMPLE 5a

According to Process I

2-[6-(5-chloro-2-thienyl)-3-methyl-7-phenyl-pyrrolo [2,1-b]thiazole-5-yl]-N-methyl sulfonyl acetamide 2-[6-(5-chloro-2-thienyl)-3-methyl-7-phenyl-pyrrolo[2, 1-b]thiazole-ethanoic acid (1.16 g, 3 mmol) is dissolved in THF (30 mL). After the addition of 1,1'-carbonyl diimidazole (CDI, 1.04 g, 6 mmol), it is stirred for 1 and then the Na-salt of methane sulfonic acid amide (1.0 g, 10 mmol), is produced by the addition of NaH (0.4 g, 80% in white oil), dropped into the solution of amide in THF (30 mL) and stirred (1 h) in the heat (50° C.). After 20 h, water is added (200 mL) and the mixture is acidified (pH1) with HCl (3N). The ether extract (200 mL) of the aqueous phase is dried ($Na_2SO_4$) and reduced, the residue is crystallized from diisopropyl ether: 0.9 g, 65%, melting point 203–204° C.

$C_{20}H_{17}ClN_2O_3S_3$ (MG=465.01).

IR ($cm^{-1}$): 3430, 3175, 3161, 1678, 1596, 1466, 1438, 1341, 1133.

$^1$H-NMR (200 MHz, $CDCl_3$): 8.2–7.7 (b, NH), 7.40–7.1 (m, 5H, arom.), 6.90 (d, 1H, J=4.0 Hz, thien.), 6.69 (d, 1H, J=4.0 Hz, thien.), 6.38 (s, 1H, thiaz., J=1.0 Hz,), 4.07 (s, 2H, $CH_2$), 3.271 (s, 3H, $SO_2CH_3$), 2.554 (q, 3H, J=1.0 Hz, $CH_3$).

EXAMPLE 6

2-[6-(4-chlorophenyl)-3,3-dimethyl-7-phenyl-2,3-dihydro-pyrrolo[2,1-b]thiazole-5-yl]-ethanoic acid (syn.: 5-carboxylmethylene-6-(4-chlorophenyl)-3,3-dimethyl-7-phenyl-2,3-dihydropyrrolo[2,1-b]thiazole)

Process A2)

A) 3-hydroxy-2-methyl-2-phenylacetamidopropane

From 2-amino-2-methyl propanol (0.12 mol) and phenyl ethanoic acid chloride (0.1 mol) in aqueous 10% NaOH (Schotten Baumann):

$C_{12}H_{17}NO_2$ (MG=207.3).

$^1$H-NMR (200 MHz, $CDCl_3$): 7.40–7.20 (m, 5H, arom.), 5.67 (b, 1H, NH), 3.53 (s, 4H, $CH_2$), 2.10 (b, 1H, —OH), 1.205 (s, 6H, $2CH_3$).

$^{13}$C-NMR (50 MHz, $CDCl_3$): 24.5, 44.2, 56.2, 70.46, 127.4, 129.0, 134.8, 172.2.

B) 2-benzyl-4,4-dimethyl-4,5-dihydro-thiazole

From 3-hydroxy-2-methyl-2-phenylacetamidopropane with phosporus pentasulfide analogous to a known process (Thewalt, K., Renkhoff, G., Fette, Seifen, Anstrichm. [fats, soaps, painting], 1968, 70(9), 648–653.

$C_{12}H_{15}NS$ (MG=205.3).

$^1$H-NMR (200 MHz, $CDCl_3$): 7.40–7.10 (m, 5H, arom.), 3.776 (s, 2H, $CH_2$), 3.053 (s, 2H, —$CH_2$), 1.372 (s, 6H, 2 $CH_3$).

$^{13}$C-NMR (50 MHz, $CDCl_3$): 27.5, 40.9, 45.6, 78.2, 127.1, 128.6, 128.9, 136.2, 166.3.

C) 2-(2-benzyl-4,4-dimethyl-4,5-dihydrothiazole-3-yl)-1-(4-chlorophenyl)-ethanonium bromide 2-benzyl-3-[2-(4-chlorophenyl)-2-oxo-ethyl]-3,3-dimethyl-2,3-dihydro-thiazolium bromide Not isolated: analogous to example 1, letter B), the leathery, dark mass of the raw product was directly cyclized by the addition of triethylamine: SC (EE, hexane 1:5), $Al_2O_3$: 37% yield.

D) 6-(4-chlorophenyl)-3,3-dimethyl-7-phenyl-2,3-dihydropyrrolo[2,1-b]thiazole $C_{20}H_{18}ClNS$ (MG=339.89).

Melting point 151–153° C.

IR ($cm^{-1}$): 1597, 1515, 1478, 1364, 1180, 1084, 1009, 825, 750, 689.

$^1$H-NMR (200 MHz, $CDCl_3$): 7.26–7.13 (m, 9H, 2 arom.), 6.753 (d, J=0.9 Hz, 1H, pyrr.), 3.489 (d, J=1.9 Hz, 2H, $CH_2$), 1.590 (s, 6H, 2 $CH_3$).

$^{13}$C-NMR (50 MHz, $CDCl_3$): 135.02, 134.59, 131.40, 129.39 (2C), 128.31 (2C), 128.28 (2C), 128.25 (2C), 127.69, 126.73, 125.34, 114.27, 112.33, 62.54, 48.04, 26.27 (2C).

E) 2-[6-(4-chlorophenyl)-3,3-dimethyl-7-phenyl-2,3-dihydro-pyrrolo[2,1-b]thiazole-5-yl]-2-oxo-ethanoic acid-ethyl ester $C_{24}H_{22}ClNO_3S$ (MG=439.96).

$^1$H-NMR (200 MHz, $CDCl_3$): 2 isomers, cis/trans: 7.32–7.11 (m, 7H) 7.00–6.89 (m, 2H), 3.683/3.676 (2 s, 2H, $CH_2$), 3.556/3.455 (q, 2H, J=7.1 Hz, $CH_2$), 1.865 (s, 6H, 2 $CH_3$), 1.090/1.046 (t, 3H, J=7.1 Hz, $CH_3$).

F) 2-[6-(4-chlorophenyl)-3,3-dimethyl-7-phenyl-2,3-dihydro-pyrrolo[2,1-b]thiazole-5-yl]-ethanoic acid 5-carboxylmethylene-6-(4-chlorophenyl)-3,3-dimethyl-7phenyl-2,3-dihydro-pyrrolo[2,1-b]thiazole $C_{22}H_{20}ClNO_2S$ (MG=397.92).

IR ($cm^{-1}$): 3423, 2932, 1714, 1617.5, 1346.3, 1091, 836.

$^1$H-NMR (200 MHz, $CDCl_3$): 7.3–7.10 (m, 9H, 2 arom.), 3.82 (s, 2H, $CH_2$), 3.465 (d, J=1.7 Hz, 2H, $CH_2$), 1.590 (s, 6H, 2 $CH_3$).

Process B2)

A) 4-(4-chlorophenyl)-1-(2-methyl-2-hydroxypropyl)-3-phenyl-1,5-dihydro-pyrrol-2-on according to directions of example 7, letter A (see below)

$C_{20}H_{20}ClNO_2$ (MG=341.84).

IR ($cm^{-1}$): 3420, 1660, 1631, 1485, 1438, 1387, 1361, 1219, 1085, 1057, 1009, 827.

$^1$H-NMR (200 MHz, $CDCl_3$): 7.354 (s, 5H, arom.), 7.30–7.18 (AA'BB', 4H, arom.), 5.30 (b, 1H, OH), 4.359 (s, 2H, $CH_2$), 3.845 (b, 2H, $CH_2$OH), 1.448 (s, 6H, 2 $CH_3$).

B) Ring closure analogous to example 7, letter C: product identical to product from letter D) 1.2 g, 19% yield.

EXAMPLE 7

Process B2)

Figure 5A:
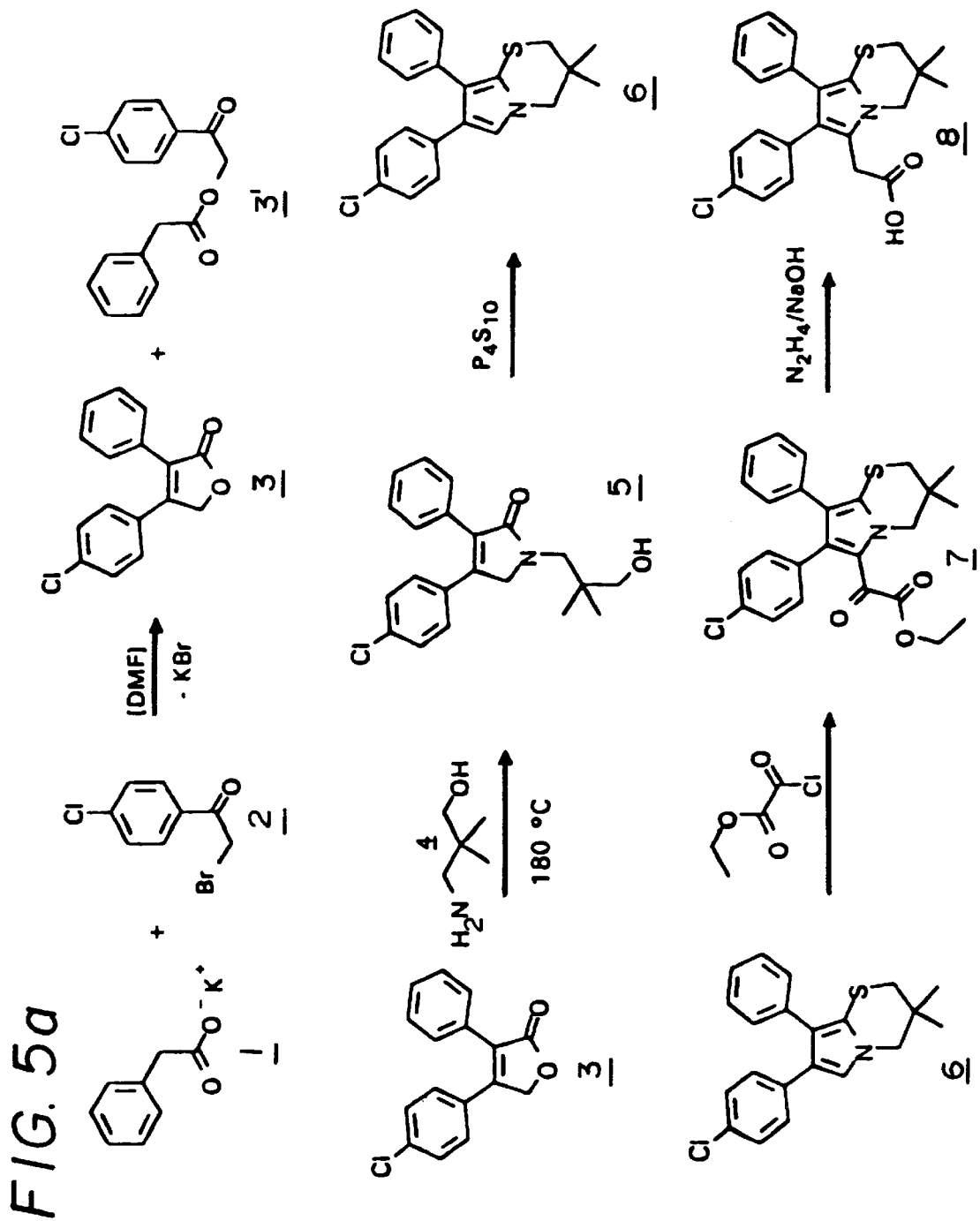
Figure 5B:
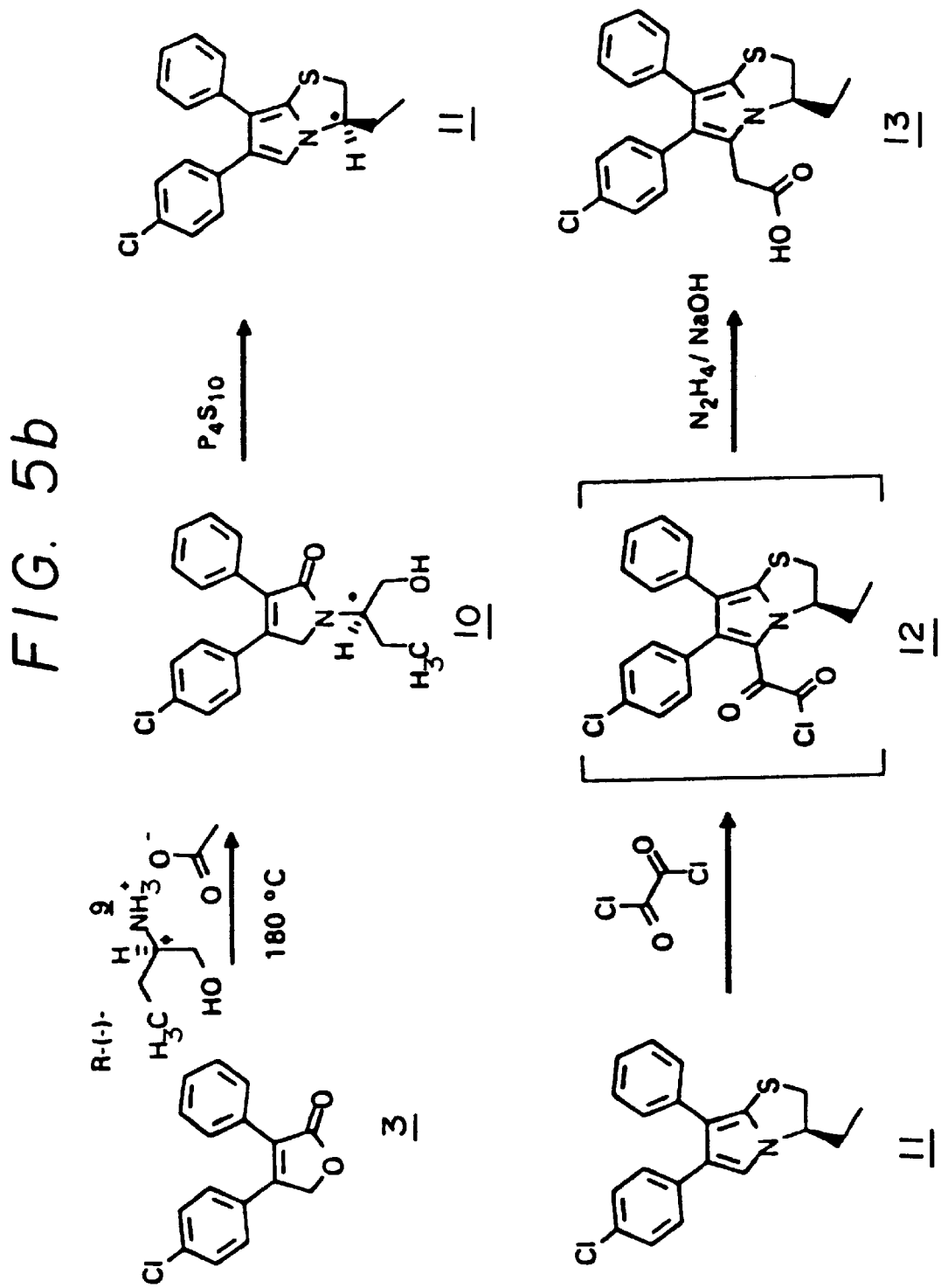

2-[6-(4-chlorophenyl)-3,3-dimethyl-7-phenyl-3,4-dihydro-2H-pyrrolo[2,1-b]1,3-thiazine-5-yl]-ethanoic acid, 8 (FIG. 5)

A) 4-(4-chlorophenyl)-3-phenyl-2(5H)-furanone (3)

Produced following known processes (a: Rio, G. and Sekiz, B. Bull. Soc. Chim. Fr. 1976, 1491, 1495. b: Padwa, A., Brookhart, T., Dehm D., and Wubbels G., J. Am. Chem. Soc. 1978, 100, 8247, 8259).

2-bromine-1-(chlorophenyl)-ethanone (2, 102.6 g, 0.44 mol) and potassium phenylacetate (1, 104.5 g, 0.6 mol) are heated to 80° C. in dimethyl formamide (600 mL) while being stirred for 4 hours and are then cooled. After the addition of water (1 L), chloroform is used for extraction (3 times 300 mL), and the chloroform extract is washed with water and then dried ($Na_2SO_4$) and concentrated to dryness. For crystallization, diisopropyl ether is added (500 mL) and the crystals, which are formed in the cold [and have] a melting point of 111–113° C., are collected (yield 92 g, 78% with reference to 2).

$C_{16}H_{11}ClO_2$ (MG=270.27).

IR ($cm^{-1}$): 1740.0, 1156.0, 1028.0, 694.

$^1$H-NMR (200 MHz, $CDCl_3$): 7.39 (s, 5H, arom.), 7.36–7.20 (AA'BB', 4H, arom.), 5.154 (s, 2H, $CH_2$).

B) 4-(4-chlorophenyl)-1-(2,2-dimethyl-3-hydroxypropyl)-3-phenyl-1,5-dihydro-pyrrol-2-on (5)
Variant A In a protective gas atmosphere (N2), a mixture of 4-(4-chlorophenyl)-3-phenyl-2(5H)-furanone (3, 26 g, 0.08 mol) and 3-hydroxy-2,2-dimethyl-propylamine (4, neopentanolamine, 80 g, 0.8 mol), while being stirred, is heated to 190–200° C. a distillation bridge set up. After 1 hour, the excess aminoalcohol is distilled off at a reduced pressure along with the water produced in the reaction. After cooling, the remaining residue is absorbed in methylene chloride and extracted with diluted hydrochloric acid (200 mL, 1N), washed with water (200 mL), dried ($Na_2SO_4$), and reduced at a lowered pressure. The remaining residue is brought to crystallization with diisopropyl ether and the crystals formed, which have a melting point of 167° C., are collected (20.2 g, 71%).

$C_{21}H_{22}ClNO_2$ (MG=355.87).

IR ($cm^{-1}$): 3375, 1657, 1487, 1450, 1401, 1156, 1089, 1047, 749.

$^1$H-NMR (200 MHz, $CDCl_3$): 7.37–7.35 (m, 5H, arom.), 7.30–7.15 (AA'BB', 4H, arom.), 4.73 (t, 1H, —OH), 4.410 (s, 2H, $CH_2N$), 3.39 (s, 2H, $CH_2N$), 3.262 (d, 2H, J=7.5 $CH_2OH$), 0.994 (s, 6H, 2 $CH_3$).

C) 7-(4-chlorophenyl)-3,3-dimethyl-8-phenyl-3,4-dihydro-2H-pyrrolo[2,1-b]1,3-thiazine (6)

At a 170–180° C. bath temperature, in a protective atmosphere of $N_2$, 4-(4-chlorophenyl)-1-(2,2-dimethyl-3-hydroxypropyl)-3-phenyl-1,5-dihydro-pyrrol-2-on (5, 10.7 g, 0.03 mol) is melted with phosphorus pentasulfide (3.33 g, 2.5 equiv., 0.015 mol), which is added in small portions until the gas development comes to a halt (1 h). Then the cooled reaction mixture is akalyzed with caustic soda (100 mL, 10%) and extracted with chloroform; the organic phase is washed with water and dried. The residue remaining after the evaporation of chloroform is crystallized from diisopropyl ether having a melting point of 147–148° C. (5.5 g, 52%).

$C_{21}H_{20}ClNS$ (MG=353.9).

IR ($cm^{-1}$): 1596, 1510, 1481, 1381, 1168, 1089, 1009, 833, 695.

$^1$H-NMR (200 MHz, $CDCl_3$): 7.4–7.00 (m, 9H, arom.), 6.758 (s, 1H, pyrr.), 3,69 (s, 2H, $CH_2N$), 2.758 (s, 2H, $CH_2S$), 1.217 (s, 6H, 2 $CH_3$).

$^{13}$C-NMR (50 MHz, $CDCl_3$): 25.9, 31.2, 37.8, 56.9, 120.6, 122.5, 125.7, 125.9, 128.0, 128.1, 128.2, 128.25, 129.2, 129.7, 130.2, 131.2, 13.5, 134.0, 134.7, 135.2.

D) 2-[7-(4-chlorophenyl)-3,3-dimethyl-8-phenyl-3,4-dihydro-2H-pyrrolo[2,1-b]1,3-thiazine-6-yl]-2-oxo-ethanoic acid-ethyl ester (7) analogous to the reaction in example 2, letter C) with oxalic acid ethyl ester chloride $C_{25}H_{24}ClNO_3S$ (MG=453.99) mixture of two isomers: cis/trans in a ratio of 4:6.

isomer a: melting point: 169° C.

IR ($cm^{-1}$): 1733, 1611, 1358, 1251, 1193, 699.

$^1$H-NMR (200 MHz, $CDCl_3$): 7.30–6.95 (m, 9H, arom.), 4.335 (s, 2H, $CH_2$), 3.552/3.470 (q, 2H, $CH_2$, J=7.2 Hz), 2.821/2.812 (s, 2H, $CH_2$), 1.259 (s, 6H, 2 $CH_3$), 1.080/1.036 (t, 3H, $CH_3$, J=7.2 Hz).

E) 2-[7-(4-chlorophenyl)-3,3-dimethyl-8-phenyl-3,4-dihydro-2H-pyrrolo[2,1-b]1,3-thiazine-6-yl]-ethanoic acid (8) analogous to example 2, letter D $C_{23}H_{22}ClNO_2S$ (MG=411.954).

Melting point: 148° C.

IR ($cm^{-1}$): 1702, 1596, 1220, 1512, 832, 698.

$^1$H-NMR (200 MHz, $CDCl_3$): 7.35–7.00 (9H, m, 2 ar.), 5.7 (b, COOH), 3.639 (s, 2H, $CH_2$), 2.747 (s, 2H, $CH_2$) 1.217 (s, 6H, 2 $CH_3$).

EXAMPLE 8

Process B2)

(R)-2-[6-(4-chlorophenyl)-3-ethyl-7-phenyl-2,3-dihydro-pyrrolo[2,1-b]thiazole-5-yl]-ethanoic acid (13, see FIG. 5)

A) (R)-4-(4-chlorophenyl)-1-(2-hydroxybutyl)-3-phenyl-1,5-dihydro-pyrrol-2-on (10)
Variant 2

Analogous to the reaction of 3,4-diphenyl-2(5H)-furanone with ammonium acetate, forming 3,4-diphenyl-1,5-dihydro-pyrrol-2-on in Rio, G. and Sekiz, B. (see above):

To melt (R)-1-hydroxy-2-butyl-ammonium acetate (9), produced by the careful mixture of R-(−)-2-amino-1-butanol (35.6 g, 0.4 mol) with equimolar quantities of glacial acetic acid (24 g, 0.4 mol), 4-(4-chlorophenyl)-3-phenyl-2(5H)-furanone (3, 11 g, 0.04 mole) is added and the mixture is heated to 180–200° C. in a distillation bridge in a protective gas atmosphere; free ethanoic acid produced is distilled off. After 1 h, it is cooled and the hardened mass is absorbed in methylene chloride (150 mL). It is washed out with water (200 mL), diluted $NaHCO_3$ (100 mL, 10%), HCl (50 mL, 1N) and water (100 mL), dried ($Na_2SO_4$), and at a lowered pressure, the solution is reduced; the remaining residue is crystallized from diethyl ether, or purified (6 g, 44%) by means of acid chromatography ($SiO_2$, diethyl ether).

$C_{20}H_{20}ClNO_2$ (MG=341.84).

Melting point 139–140° C.

IR ($cm^{-1}$): 3378, 2964, 1660, 1497, 1458, 1402, 1364, 1231, 1091, 824, 777, 751, 742.

$^1$H-NMR (200 MHz, $CDCl_3$): 7.4–7.15 (m, 9H, arom.), 4.407/4.240 (AB, $J_{AB}$=19.4 Hz), 4.4–4.0/4.0–3.7 (m, 3H, CH—$CH_2$), 3.1 (b, 1H, OH), 2.0–1.6 (m, 2H, $CH_2$), 0.991 (t, 3H, $CH_3$).

B) (R)-2-[6-(4-chlorophenyl)-3-ethyl-7-phenyl-2,3-dihydro-pyrrolo[2,1-b]thiazole (11)

At a bath temperature of 170–180° C. in a protective atmosphere of $N_2$, (R)-4-(4-chlorophenyl)-1-(2-hydroxybutyl)-3-phenyl-1,5-dihydro-pyrrol-2-on (10, 10.65 g, 0.03 mol) is melted with phosphorus pentasulfide (6.3 g, in portions) until the gas development comes to a halt (1 h). Then the cooled reaction mixture is alkalyzed with caustic soda (100 mL, 10%) and extracted with chloroform; the organic phase is washed with water and dried. The residue remaining after the evaporation of chloroform crystallizes out slowly: (3.9 g, 37%) melting temp. 58–60° C.

$C_{20}H_{18}ClNS$ (MG=339.89).

IR ($cm^{-1}$): 2926, 1700, 1594, 1520, 1386, 1170, 1084.850, 700.

$^1$H-NMR (200 MHz, $CDCl_3$): 7.50–6.90 (m, 9H, arom.), 6.807 (s, 1H, pyrrol.), 4.270 (m, 1H, CH), 3.9–3.7/3.5–3.3 (AB part in the ABX system CH—$CH_2$—, 2H), 2.3–1.6 (m, 2H, $CH_2$), 1.091 (t, 3H, $CH_3$).

C) (R)-2-[6-(4-chlorophenyl)-3-ethyl-7-phenyl-2,3-dihydro-pyrrol-[2,1-b]thiazole-5-yl]-2-oxo-ethanoic acid-ethyl ester Yellow crystals from diiosopropyl ether, 9 g, 37%.
Melting point: $C_{24}H_{22}ClNO_3S$ (MG=439.9).
$^1$H-NMR (200 MHz, CDCl$_3$): 7.35–7.10 (m, 7H, arom.), 7.05–6.95 (m, 2H, arom.), 5.34 (m, 1H, CH), 4.10–3.95/3.65–3.45 (m, 2H, AB part of the CHCH$_2$ system), 3.60 (q, 2H, J=7.2 Hz, CH$_2$), 2.1–1.7 (m, 2H, CH$_2$), 1.074 (t, 3H, CH$_3$), 1.047 (t, 3H, CH$_3$).

D) (R)-2-[6-(4-chlorophenyl)-3-ethyl-7-phenyl-2,3-dihydro-pyrrolo-[2,1-b]thiazole-5-yl]-ethanoic acid $C_{22}H_{20}ClNO_2S$ (MG=397.93).
IR (cm$^{-1}$): 3427, 1707, 1601, 1522, 1362, 1487, 1459, 1091, 835.700.
$^1$H-NMR (200 MHz, CDCl$_3$): 7.5–6.9 (m, 9H, arom.), 4.52 (m, 1H, CH) 4.05–3.85/3.5–3.35 (m, AB part of the ABX system CHCH$_2$—), 3.65–3.55 (M, C$\underline{H}_2$—CO), 2.2–1.6 (m, 2H, CHC$\underline{H}_2$CH$_3$), 1.052 (t, 3H, J=7.4 Hz, CH$_3$).

E) (S)-2-[6-(4-chlorophenyl)-3-ethyl-7-phenyl-2,3-dihydro-pyrrol-[2,1-b]thiazole-5-yl]-ethanoic acid In an analogous manner, the enantiomer to substance D) was obtained from (S)-(+) 1-hydroxy-2-butylamine:
$^1$H-NMR identical to (R)-enantiomer spectrum.
IR (cm$^{-1}$): 3427, 2965, 2931, 1707, 1601, 1522, 1091.
Melting point: 102–104° C.

EXAMPLE 9

(R,S)-6-(4-chlorophenyl)-2-methyl-7-7-phenyl-2,3-dihydro-pyrrolo-[2,1-b]thiazole A) 4-(4-chlorophenyl)-1-[(S)-1-hydroxy-2-propyl]-3-phenyl-1,5-dihydro-pyrrol-2-on produced from 3 according to process B2 analogous to example 8 (see FIG. 5), 10.6 g, 64%.

$C_{19}H_{18}ClNO_2$ (MG=327.81).
Melting point: 97.5–98.5° C. (from diisopropyl ether).
MIR (cm$^{-1}$): 3395, 1672, 1485, 1451, 1399, 1090, 826, 695.
$^1$H-NMR (200 MHz, CDCl$_3$): 7.40–7.30 (m, 5H, arom.), 7.30–7.18 (AA'BB', 4H, arom.), 4.437 (s, 2H, CH$_2$), 4.16 (m, 1H, CH) 3.70–3.50 (m, 2H, AB part of the ABX system CHCH$_2$), 3.19 (d, 1H, OH, J=4.3 Hz), 1.273 (d, 3H, CH$_3$, J=6.3 Hz).

B) (R,S)-6-(4-chlorophenyl)-2-methyl-7-phenyl-2,3-dihydro-pyrrolo-[2,1-b]thiazole (after SC purification to SiO$_2$ with EE/hexane (2:8): leathery mass, no crystallization, 4.8 g, 50% racemate.).

$C_{19}H_{16}ClNS$ (MG=325.86).
IR (cm$^{-1}$): 1697, 1594, 1516, 1479, 1440, 1391, 1369, 1087, 1008, 829, 694.
$^1$H-NMR (200 MHz, CDCl$_3$): 7.4–7.0 (m, 9H, 2 arom.), 6.79 (s, 1H, pyrr.), 4.5–4.2/4.1–3.7 (m, 2H, AB part of the ABX system CHC$\underline{H}_2$), 3.82 (m, 1H, CH) 1.61–1.54 (m, 3H, CH$_3$, J=6.3 Hz, J=0.6 Hz).

EXAMPLE 10

2-[6-(4-chlorophenyl)-3,3-dimethyl-1,1-dioxo-7-phenyl-2,3-dihydro-pyrrolo[2,1-b]thiazole 6-(4-chlorophenyl)-3,3-dimethyl-7-phenyl-2,3-dihydro-pyrrolo[2,1-b]thiazole, produced according to process B2, as described in example 6 (340 mg, 1 mmol) and dissolved in methylene chloride, (50 mL) is dropped into the dried (Na$_2$SO$_4$)-solution of m-chloroperbenzoic acid (850 mg, 55%, 2.5 mmol) in methylene chloride. Cooked with recycling, it is stirred until according to the thin-layered chromatographical control (SiO$_2$, CH$_2$Cl$_2$) of the reaction, no more educt (Rf=0.95) can be detected and primarily produced sulfoxide (Rf=0.1) has been transformed into sulfone (RF=0.3) to the greatest extent possible (16 h). The purification is carried out via column chromatography on neutral Al$_2$O$_3$ (Akt. II) with diethyl ether as eluent: sulfone (Rf=0.75, 230 mg), sulfoxide (Rf=0.5, 30 mg).

$C_{20}H_{18}ClNO_2S$ (MG=371.89).
$^1$H-NMR (200 MHz, CDCl$_3$): 7.36–7.22 (m, 5H, arom.), 7.28–7.20/7.18–7.10 (AA'BB', 4H, arom), 6.91 (s, 1H, pyrr.), 3.755 (s, 2H, CH$_2$SO$_2$), 1.804 (s, 6H, 2 CH$_3$).

EXAMPLE 11

(R,S)-2-[6-(4-chlorophenyl)-3,3-dimethyl-1-oxo-7-phenyl-2,3-dihydro-pyrrolo[2,1-b]-thiazole Obtained according to process B2) from 2-[6-(4-chlorophenyl)-3,3-dimethyl-7-phenyl-2,3-dihydro-pyrrolo [2,1-b]-thiazole Analogous to example 10: The sulfoxide is predominantly produced when lower quantities of m-chloroperbenzoic acid are used (1.2 equivalents, 400 mg) and work is carried out at lower temperatures (–20° C., 2 h).

The purification is carried out as described in example 10, by means of SC on neutral Al$_2$)$_3$ (Akt. II) with diethyl ether as eluent: educt (20 mg), sulfone (80 mg), sulfoxide (170 mg).

$C_{20}H_{18}ClNO_S$ (MG=355.89).
$^1$H-NMR (200 MHz, CDCl$_3$): 7.45–7.30 (m, 5H, arom.), 7.35–7.20/7.20–7.15 (AA'BB', 4H, arom.), 6.95 (s, 1H, pyrr.), 3.60/3.48 (AB, 2H, J=13.6 Hz, CH$_2$SO), 1.937 (s, 3H, CH$_3$), 1.713 (s, 3H, CH$_3$).

The combined compounds were obtained in an analogous manner according to the corresponding processes from FIGS. 1 to 5. The compounds from examples 1 to 11 were likewise contained in the table.

Formula I

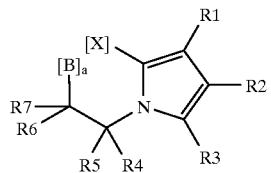

| Example | X | [B]$_a$ | R1 | R2 | R3 | R4 | R5 | R6 | R7 | Process |
|---|---|---|---|---|---|---|---|---|---|---|
| 1 | N—Ph | — | Ph | Ph | CH$_2$—COOH | H | H | H | H | A1/D |
| 2 | S | — | Ph | 4-Cl—Ph | CH$_2$—COOH | CH$_3$ | — | H | — | A3/C (Var A) |
| 3 | S | — | H | 4-Cl—Ph | CH$_2$—COOH | CH$_3$ | — | H | — | A3/D |
| 4 | S | — | Ph | 4-Cl—Ph | CH$_2$—COOH | CH$_3$ | — | CH$_3$ | — | A3/C (Var A) |
| 5 | S | — | Ph | 5-Chlor-2-thien. | CH$_2$—COOH | CH$_3$ | — | H | — | A3/C (Var D) |
| 5b | S | — | Ph | 5-Chlor-2-thien. | CH$_2$—CONHSO$_2$CH$_3$ | CH$_3$ | — | H | — | I |
| 6 | S | — | Ph | 4-Cl—Ph | CH$_2$—COOH | CH$_3$ | CH$_3$ | H | H | A2 o. B2/C (Var A) |
| 7 | S | CH$_2$ | Ph | 4-Cl—Ph | CH$_2$—COOH | H | H | CH$_3$ | CH$_3$ | B2/C (Var. A) |
| 8 | S | — | Ph | 4-Cl—Ph | CH$_2$—COOH | C$_2$H$_5$ | H | H | H | B2/C (Var A/B) |
| 9 | S | — | Ph | 4-Cl—Ph | H | H | H | CH$_3$ | H | B2 |
| 10 | SO | — | Ph | 4-Cl—Ph | H | CH$_3$ | CH$_3$ | H | H | A2/N |
| 11 | SO$_2$ | — | Ph | 4-Cl—Ph | H | CH$_3$ | CH$_3$ | H | H | A2/N |
| 12 | SO$_2$ | CH$_2$ | Ph | 4-Cl—Ph | H | H | H | CH$_3$ | CH$_3$ | B2/N |
| 13 | SO | CH$_2$ | Ph | 4-Cl—Ph | H | H | H | CH$_3$ | CH$_3$ | B2N |
| 14 | S | — | Ph | 4-Cl—Ph | H | H | COOH | H | H | A2 |
| 15 | S | — | Ph | 4-Cl—Ph | H | H | COOH | CH$_3$ | CH$_3$ | A2 |
| 16 | S | — | H | 4-Cl—Ph | CH$_2$COOH | CH$_3$ | — | CH$_3$ | — | A/C (Var. B) |
| 17 | S | — | H | 4-Cl—Ph | CH$_2$COOH | H | H | H | H | A/D |
| 18 | N—CH$_3$ | CH$_2$ | Ph | 4-Cl—Ph | CH$_2$COOH | H | H | H | H | A2/D |
| 19 | N—CH$_3$ | — | Ph | Ph | CH$_2$—COOH | H | H | H | H | A2/D |

We claim:

1. A heterocyclic compound of formula I:

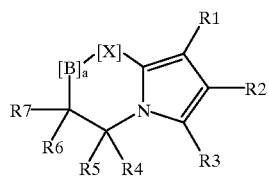

in which two of the radicals $R^1$, $R^2$, and $R^3$, which may be identical or different, stand for an aryl radical, which optionally has one or two substituents selected from the group comprising halogen, CN, CF$_3$, NO$_2$, OH, alkoxy, OCF$_3$, alkyl, and aryloxy, or a monocyclic or bicyclic, aromatic, heterocyclic radical, which has at least one oxygen, nitrogen, and/or sulfur atom and which is optionally condensed with a phenyl or naphthyl radical and optionally substituted by halogen, CF$_3$, alkyl, or alkoxy, and the third of the radicals $R^1$, $R^2$, and $R^3$ stands for H, CHO, CO$_2$H, COO alkyl, COS alkyl, COCO$_2$H, COCO$_2$, alkyl, or A—Y, A stands for C$_1$–C$_8$ alkylene or C$_2$–C$_8$ alkenylene, Y stands for CO$_2$H, SO$_3$H, OPO(OH)$_2$, PO(OH)$_2$, tetrazolyl, COO alkyl, SO$_2$O alkyl, CHO, OH, or CONR$^8$R$^9$, $R^8$ and $R^9$, which may be identical or different, stand for H, alkyl, OH, acyl, SO$_2$ alkyl, or SO$_2$ phenyl, where the alkyl radical of the sulfonyl group is optionally substituted by one or more halogen atoms and the aryl radical is optionally substituted by one or more halogen, C$_1$–C$_8$ alkyl, or C$_1$–C$_8$ alkoxy radicals, $R^4$, $R^5$, $R^6$, and $R^7$, which may be identical or different, stand for H, alkyl, Y, or A—Y, or two of the vicinal radicals stand for a chemical bond between the two ring atoms to which they are bonded, and the other two have the meanings stated or two of the geminal radicals, together with the carbon atom to which they are bonded, stand for a carbonyl group or thiocarbonyl;

X stands for O, S, SO, SO$_2$, or NR$^{10}$, where R$^{10}$ stands for H, alkyl, A—Y or aryl selected from the group consisting of phenyl and naphthyl wherein said aryl is optionally substituted by halogen, C$_1$–C$_8$ alkyl or C$_1$–C$_8$ alkoxy, B stands for CR$^{11}$R$^{12}$, where R$^{11}$ and R$^{12}$, which may be identical or different, stand for H, alkyl, Y, or A—Y, and A and Y have the meanings stated, or R$^{11}$ and R$^{12}$, together with the carbon to which they are bonded, stand for a carbonyl group or thiocarbonyl, and a stands for 0 or 1, and their optical isomers, salts, and esters, with the proviso that compounds of formula I wherein a is 0, $R^1$ is hydrogen, $R^2$ and $R^3$ are phenyl, X is NR$^{10}$ and R$^{10}$ is ethyl are excluded.

2. Formula I compounds according to claim 1, in which two of the radicals $R^1$, $R^2$, and $R^3$ independently stand for a phenyl radical, a phenyl radical substituted by one to three halogen atoms or a 5- or 6-membered, monocyclic, aromatic heterocyclic radical which has at least one oxygen, nitrogen, and/or sulfur atom and which can be optionally substituted by a halogen atom, and the third of the radicals $R^1$, $R^2$, and $R^3$ stands for A—Y, A stands for C$_1$–C$_8$ alkylene and Y stands for CO$_2$H, COOC$_1$–C$_8$ alkyl, SO$_3$H, SO$_2$OC$_1$–C$_8$ alkyl, CHO.

3. A method for the prevention of allergically induced disease or for the treatment of diseases of the rheumatoid variety which comprises administering a pharmaceutically effective amount of the compound of claim 1 to a human or mammalian subject.

4. Formula I compounds according to claim 2, in which $R^1$ stands for H or phenyl, $R^2$ stands for phenyl or halogen-substituted phenyl.

5. Formula I compounds according to claim 1, in which one or two of the radicals $R^1$, $R^2$, and $R^3$ stands for a 5- or 6-membered aromatic, heterocyclic radical, which, as defined in claim 1, is optionally substituted and condensed.

6. Compounds according to claim 5, where the heterocyclic radical is a thiophene, pyrrole, imidazole, thiazole, thiadiazole, furan, oxazole, isoxazole, pyridine, pyrimidine, benzofuran, or quinoline radical.

7. Compounds according to claim 1, having the formula

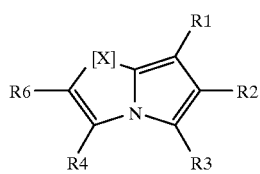

I' and

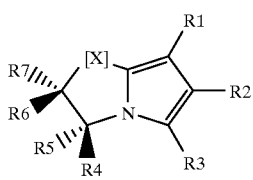

I"

in which X, $R^1$, $R^2$, $R^3$, $R^4$, $R^5$, $R^6$, and $R^7$ have the meanings indicated in claim 1.

8. Formula I' compounds according to claim 7, in which X stands for S, $R^1$ stands for H or phenyl, R2 stands for 4-chlorophenyl or 5-chloro-2-thienyl; $R^3$ is A—Y, and $R^4$ and $R^6$ stand for H or methyl;
or
formula I' compounds according to claim 7, in which X stands for S, SO, or $SO_2$, $R^1$ stands for phenyl, $R^2$ stands for 4-chlorophenyl, and $R^3$ is A—Y, and the radicals $R^4$, $R^5$, $R^6$, and $R^7$ stand for H or methyl.

9. A pharmaceutical agent containing at least one compound according to claim 1, if need be in combination with pharmaceutically compatible vehicles and/or additives.

10. The compound of claim 8 wherein A—Y is —$CH_2COOH$.

11. A process for producing the compounds according to claim 1 wherein a compound with the general formula II:

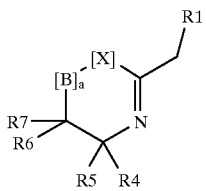

is reacted with a compound having the general formula III:

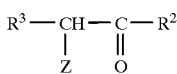

III where in the above formulas, two of the radicals $R^1$, $R^2$, and $R^3$ have the meanings indicated in claim 1 and the third stands for a hydrogen atom and Z stands for Cl or Br, thereby forming a compound with the general formula Ia:

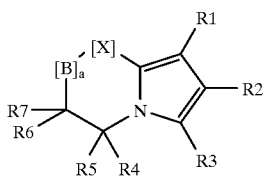

Ia in which $R^1$ to $R^7$, B, a, and X have the meanings stated in claim 1 and optionally inserting a radical into the compound of formula Ia, wherein said radical corresponds to the meaning of the third of the radicals $R^1$, $R^2$, and $R^3$ as defined in claim 1.

12. The process according to claim 11, characterized in that for the production of the formula I compounds, in which the third of the radicals $R^1$, $R^2$, and $R^3$ stands for $CH_2COOH$, $CH_2COO$ alkyl, or $COCO_2H$, a formula Ia compound defined in claim 11.

a) is reacted with oxalyl chloride, producing a formula I compound, in which one of the radicals $R^1$, $R^2$, and $R^3$ stands for $COCO_2H$, and if so desired, this compound is treated with a reagent that is suited for the reduction of the keto group of ketocarboxylic acid to a $CH_2$ group so that a formula I compound is obtained in which one of the radicals $R^1$, $R^2$, and $R^3$ stands for $CH_2CO_2H$, b) is reacted with a diazoethanoic acid alkyl ester, producing a formula I compound, in which one of the radicals $R^1$, $R^2$, and $R^3$ stands for $CH_2COO$ alkyl, and if so desired, the compound produced undergoes an ester cleavage in order to obtain a formula I compound in which one of the radicals $R^1$, $R^2$, and $R^3$ stands for $CH_2CO_2H$, or c) is reacted with chloral, producing a formula I compound, in which one of the radicals $R^1$, $R^2$, and $R^3$ stands for —$CH(OH)CCl_3$ and the compound obtained is transformed into an activated derivative and this is reduced with dithionite to a formula I compound in which one of the radicals $R^1$, $R^2$, and $R^3$ stands for $CH_2COOH$.

13. A process for producing the compounds according to claim 1, in which X stands for O or S, characterized a formula VI compound:

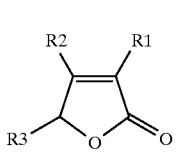

VI in which $R^1$, $R^2$, and $R^3$ have the meanings indicated in claim 1, is reacted with with a compound with the formula

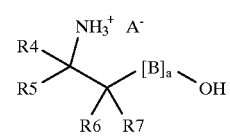

in which $A^-$ stands for an anion, B, a, and $R^4$ to $R^7$ have the meanings mentioned in claim 1, to form a formula VII compound:

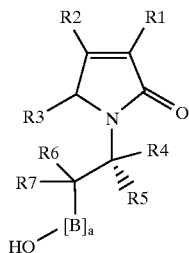

VII and the formula VII compound is cyclized into a compound with the formula

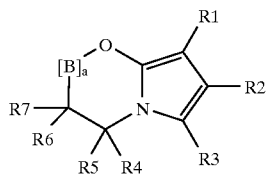

preferably with the aid of polyphosphoric acid, or a formula VII compound, in the presence of phosporus pentasulfide, is cyclized into a compound with the formula

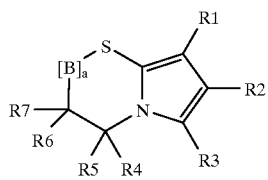

14. A process for producing the compounds according to claim 7 of formula I', wherein a formula VI compound is reacted with a compound having the formula

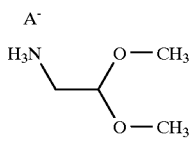

in which $A^-$ stands for an anion, producing a formula VIII compound

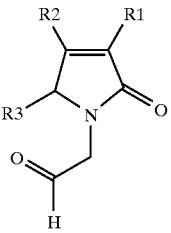

VIII and a) a formula VIII compound is cyclized to produce a formula I' compound, in which X stands for O, preferably with the aid of polyphosphoric acid (PPA), or b) a formula VIII compound is cyclized with phosphorous pentasulfide to produce a formula I' compound, in which X stands for S, or c) a formula VIII compound is cyclized with a compound with the formula $R^{10}$—$NH_3+$ to produce a formula I' compound, in which X stands for N—$R^{10}$; with the proviso that the compound of formula VI has the formula:

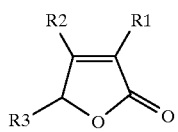

VI in which two of the radicals $R^1$, $R^2$, and $R^3$, which may be identical or different, stand for an aryl radical, which optionally has one or two substituents selected from the group comprising halogen, CN, $CF_3$, $NO_2$, OH, alkoxy, $OCF_3$, alkyl, and aryloxy, or a monocyclic or bicyclic, aromatic, heterocyclic radical, which has at least one oxygen, nitrogen, and/or sulfur atom and which is optionally condensed with a phenyl or naphthyl radical and optionally substituted by halogen, $CF_3$, alkyl, or alkoxy, and the third of the radicals $R^1$, $R^2$, and $R^3$ stands for H, CHO, $CO_2H$, COO alkyl, COS alkyl, $COCO_2H$, $COCO_2$, alkyl, or A—Y, A stands for $C_1$-$C_8$ alkylene or $C_2$-$C_8$ alkenylene, Y stands for $CO_2H$, $SO_3H$, $OPO(OH)_2$, $PO(OH)_2$, tetrazolyl, COOalkyl, $SO_2O$ alkyl, CHO, OH, or $CONH^8R^9$, $R^8$ and $R^9$, which may be identical or different, stand for H, alkyl, OH, acyl, $SO_2$ alkyl, or $SO_2$ phenyl, where the alkyl radical of the sulfonyl group is optionally substituted by one or more halogen atoms and the aryl radical is optionally substituted by one or more halogen, $C_1$-$C_8$ alkyl, or $C_1$-$C_8$ alkoxy radicals.

15. A compound as claimed in claim 1 wherein X is S, a is O, $R^1$ is phenyl, $R^2$ is 4-chlorophenyl, $R^3$ is $CH_2$—$CO_2H$, $R^4$ is $CH_3$, $R^5$ is $CH_3$, $R^6$ is hydrogen, and $R^7$ is hydrogen.

* * * * *